(12) United States Patent
Baram et al.

(10) Patent No.: US 11,680,257 B2
(45) Date of Patent: *Jun. 20, 2023

(54) SYSTEMS AND METHODS FOR GROWING A BIOFILM OF PROBIOTIC BACTERIA ON SOLID PARTICLES FOR COLONIZATION OF BACTERIA IN THE GUT

(71) Applicant: MYBIOTICS PHARMA LTD., Rehovot (IL)

(72) Inventors: David Baram, Nir-Zvi (IL); Rachel Diamant, Ein-Vered (IL); David Daboush, Mishmar David (IL)

(73) Assignee: MYBIOTICS PHARMA LTD., Rehovot (IL)

( * ) Notice: Subject to any disclaimer, the term of this patent is extended or adjusted under 35 U.S.C. 154(b) by 33 days.

This patent is subject to a terminal disclaimer.

(21) Appl. No.: 17/031,271

(22) Filed: Sep. 24, 2020

(65) Prior Publication Data

US 2021/0009985 A1    Jan. 14, 2021

Related U.S. Application Data

(63) Continuation of application No. 15/572,972, filed as application No. PCT/IB2016/000933 on May 9, 2016, now Pat. No. 10,793,847.

(60) Provisional application No. 62/159,849, filed on May 11, 2015, provisional application No. 62/159,846, filed on May 11, 2015.

(51) Int. Cl.
| | |
|---|---|
| C12N 11/02 | (2006.01) |
| C12N 1/20 | (2006.01) |
| A61K 35/747 | (2015.01) |
| C12N 11/12 | (2006.01) |
| C12N 11/14 | (2006.01) |
| A61K 35/74 | (2015.01) |
| A61K 9/14 | (2006.01) |
| A61K 35/741 | (2015.01) |
| A61K 35/00 | (2006.01) |
| C12N 11/06 | (2006.01) |
| C12N 11/04 | (2006.01) |

(52) U.S. Cl.
CPC .............. *C12N 11/02* (2013.01); *A61K 9/141* (2013.01); *A61K 35/74* (2013.01); *A61K 35/741* (2013.01); *A61K 35/747* (2013.01); *C12N 1/20* (2013.01); *C12N 11/04* (2013.01); *C12N 11/12* (2013.01); *C12N 11/14* (2013.01); *A61K 2035/11* (2013.01); *A61K 2035/115* (2013.01)

(58) Field of Classification Search
CPC .......... C12N 11/02; C12N 1/20; C12N 11/04; C12N 11/12; C12N 11/14; A61K 9/141; A61K 35/74; A61K 35/741; A61K 35/747; A61K 2035/11; A61K 2035/115

See application file for complete search history.

(56) References Cited

U.S. PATENT DOCUMENTS

| | | |
|---|---|---|
| 4,250,169 A | 2/1981 | Hosoi et al. |
| 5,443,826 A | 8/1995 | Borody |
| 6,210,715 B1 | 4/2001 | Starling et al. |
| 7,972,840 B2 | 7/2011 | Hasegawa et al. |
| 8,357,498 B2 | 1/2013 | Ushiyama et al. |
| 8,673,606 B2 | 3/2014 | Menashe |
| 9,216,158 B2 | 12/2015 | Menashe |
| 9,308,226 B2 | 4/2016 | Borody |
| 9,962,413 B2 | 5/2018 | Borody |
| 10,022,406 B2 | 7/2018 | Borody |
| 10,064,899 B1 | 9/2018 | Borody |
| 10,119,116 B2 | 11/2018 | Subhadra |
| 10,138,460 B2 | 11/2018 | Subhadra |
| 10,172,793 B2 | 1/2019 | Henriksen et al. |
| 10,258,567 B1 | 4/2019 | Krebs-Bensch |
| 10,278,997 B2 | 5/2019 | Borody |
| 10,328,107 B2 | 6/2019 | Borody |
| 10,463,702 B2 | 11/2019 | Borody |
| 10,610,551 B2 | 4/2020 | Borody |

(Continued)

FOREIGN PATENT DOCUMENTS

| | | |
|---|---|---|
| CN | 101368154 A | 2/2009 |
| CN | 101440395 A | 5/2009 |

(Continued)

OTHER PUBLICATIONS

Cheow et al., Carbohydrate Polymers, 2014, vol. 103, p. 587-595, available online Jan. 21, 2014.*

Lim, Kieran F., "Negative pH Does Exist.", Journal of Chemical Education, vol. 83, No. 10: p. 1465, 2006.

Sara E. Jones et al., "Probiotic Lactobacillus reuteri biofilms produce antimicrobial and anti-inflammatory factors", BMC Microbiology, vol. 9, pp. 35-43, 2009.

Gordon Ramage et al., "A seed and feed model for the formation of Cndida albicans biofilms under flow conditions using an inproved modified Robbins device" Revista Iberoamericana de Micologia, vol. 25, No. 1, pp. 37-40, 2008.

(Continued)

*Primary Examiner* — Kade Ariani
(74) *Attorney, Agent, or Firm* — The Roy Gross Law Firm, LLC; Roy Gross

(57) ABSTRACT

The present invention provides a method, wherein the method forms a biofilm, wherein the biofilm comprises a population of at least one bacterial strain attached to particles, wherein the biofilm is configured to colonize a gut of a subject in need thereof for at least five days, when ingested by the subject, the method comprising: a. obtaining a population comprising at least one strain of bacteria; b. inoculating a growth medium containing particles with the population comprising at least one strain of bacteria; c. incubating the particles with the population comprising at least one bacterial strain for a time sufficient for the population of at least one strain of bacteria to attach to the particles; and d. culturing the population comprising at least one strain of bacteria attached to the particles in a growth medium, for a time sufficient to form a biofilm.

18 Claims, 13 Drawing Sheets

(56) References Cited

U.S. PATENT DOCUMENTS

| | | |
|---|---|---|
| 10,675,309 B2 | 6/2020 | Borody |
| 11,123,383 B2 | 9/2021 | Baram et al. |
| 11,173,183 B2 | 11/2021 | Borody |
| 11,207,356 B2 | 12/2021 | Borody |
| 2003/0119157 A1 | 6/2003 | Jeong et al. |
| 2003/0147858 A1 | 8/2003 | Renaud et al. |
| 2004/0101906 A1 | 5/2004 | Lacroix et al. |
| 2004/0223956 A1 | 11/2004 | Naidu et al. |
| 2005/0277107 A1 | 12/2005 | Toner et al. |
| 2007/0178078 A1 | 8/2007 | Khoo |
| 2009/0162323 A1 | 6/2009 | Boehm et al. |
| 2012/0129693 A1 | 5/2012 | Ano |
| 2012/0237489 A1 | 9/2012 | Heil |
| 2012/0247993 A1 | 10/2012 | Palazzi et al. |
| 2013/0022575 A1 | 1/2013 | Cassity |
| 2013/0211100 A1 | 8/2013 | Palsson et al. |
| 2014/0147417 A1 | 5/2014 | Sadowsky et al. |
| 2014/0363398 A1 | 12/2014 | Jones et al. |
| 2014/0370107 A1 | 12/2014 | Mogna et al. |
| 2017/0173091 A1 | 6/2017 | Lynch |
| 2019/0209626 A1 | 7/2019 | Li et al. |
| 2019/0210935 A1 | 7/2019 | Belcher et al. |
| 2021/0079356 A1 | 3/2021 | Novak et al. |
| 2021/0205375 A1 | 7/2021 | Borody |
| 2022/0023356 A1 | 1/2022 | Borody |

FOREIGN PATENT DOCUMENTS

| | | |
|---|---|---|
| CN | 105193856 A | 12/2015 |
| DE | 202013103204 U1 | 7/2013 |
| EP | 1137423 B1 | 10/2001 |
| EP | 1880727 A2 | 1/2008 |
| JP | 2006204296 A | 8/2006 |
| JP | 2011000120 A | 1/2011 |
| JP | 2018517430 A | 7/2018 |
| RU | 2580002 C1 | 10/2016 |
| WO | 2004022698 A2 | 3/2004 |
| WO | 2005095656 A1 | 10/2005 |
| WO | 2009092810 A2 | 7/2009 |
| WO | 2010054439 A1 | 5/2010 |
| WO | 2010103374 A2 | 9/2010 |
| WO | 2010118857 A2 | 10/2010 |
| WO | 2010137404 A1 | 12/2010 |
| WO | 2011033310 A1 | 3/2011 |
| WO | 2011094027 A1 | 8/2011 |
| WO | 2012101500 A1 | 8/2012 |
| WO | 2014197562 A1 | 12/2014 |
| WO | 2015134808 A2 | 9/2015 |
| WO | 2016181228 A2 | 11/2016 |
| WO | 2017095968 A1 | 6/2017 |
| WO | 2017208237 A1 | 12/2017 |
| WO | 2018013583 A2 | 1/2018 |
| WO | 2020086487 A1 | 4/2020 |
| WO | 2020180037 A1 | 9/2020 |
| WO | 2020212297 A1 | 10/2020 |
| WO | 20211247571 A1 | 12/2021 |

OTHER PUBLICATIONS

I. Cleenwerck et al., "Re-examination of the genus *Acetobacter*, with descriptions of *Acetobacter cerevisiae* sp. nov. and *Acetobacter malorum* sp. nov.", International Journal of Systematic and Evolutionary Microbiology, vol. 52, Pt. 5, pp. 1551-1558, 2002.

Ingegerd Adlerberth et al., "A Mannose-Specific Adherence Mechanism in Lactobacillus plantarum Conferring Binding to the Human Colonic Cell Line HT-29", Applied and Environmental Microbiology, vol. 62, No. 7, pp. 2244-2251, 1996.

Seung Chul Shin et al., "*Drosophila* Microbiome Modulates Host Developmental and Metabolic Homeostasis via Insulin Signaling", Science, vol. 334, No. 6056, pp. 670-674, 2011.

Wean Sin Cheow et al., "Controlled release of Lactobacillus rhamnosus biofilm probiotics from alginate-locust bean gum microcapsules", Carbohydrate Polymers, vol. 103, pp. 587-595, 2014.

Cheow et al., "Biofilm-Like Lactobacillus rhamnosus Probiotics Encapsulated in Alginate and Carrageenan Microcapsules Exhibiting Enhanced Thermotolerance and Freeze-Drying Resistance", Biomacromolecules, Sep. 9, 2013, vol. 14, No. 9, pp. 3214-3222.

Tonnesen et al., Alginate in Drug Delivery Systems, Drug Development and Industrial Pharmacy, 28(6), 621-630 (2002).

Ferhan Ozadali, Development of a biofilm bioreactor for enhanced propionic and acetic acid production, Ph.D. Thesis 1997, "Development of a biofilm bioreactor for enhanced propionic and acetic acid production", Iowa State University, 1997.

Liu et al., Water Research, 2002, vol. 36, p. 1653-1665.

Mantere-Alhonen, S., Lait, INRA Editions, 1995, vol. 75 (4-5), p. 447-452.

Tonnesen et al., Drug Development and Industrial Pharmacy, 2002, vol. 28, No. 6, p. 621-630.

PCT Preliminary Report on Patentability for International Patent Application No. PCT/IB2016/000933, dated Nov. 14, 2017, 6 pp.

PCT Search Report for International Patent Application No. PCT/IB2016/000933, dated Nov. 2, 2016, 2 pp.

PCT Written Opinion for International Patent Application No. PCT/IB2016/000933, dated Nov. 2, 2016, 5 pp.

Google (Scholar) search results for "bacteria biofilm culture particle under shear force", internet source [retrieved Apr. 29, 2020], 4 pp.

Google search results for "biofilm immobilized particle bacteria attach", internet source [retrieved Sep. 10, 2020], 8 pp.

Weng-Tat Chan et al., "A comparison and optimization of methods and factors affecting the transformation of *Escherichia coli*", Bioscience Reports, 33(6), pp. 931-937, 2013.

Doron S, Snydman DR., "Risk and Safety of Probiotics", Clinical Infectious Diseases, 60 (Suppl 2), S129-S134, 2015.

Kozlova NM et al., "Inflammatory diseases of the upper digestive tract (pathogenesis, clinical picture, diagnosis, treatment)". Manual for doctors. Irkutsk 2012. Found online https: //www.ismu.baikal.ru/src/downloads/b58cd1df_vospalitelnye_zabolevaniya_verhnih_otdelov_zhkt.pdf. Date of access Jan. 13, 2021, Table 1 on pp. 9-10).

Kapoore et al., "Co-culturing microbial consortia: approaches for applications in biomanufacturing and bioprocessing" Critical Reviews in Biotechnology 2021, 27 pages.

Atarashi et al., "Treg induction by a rationally selected mixture of Clostridia strains from the human microbiota" Nature 2013, vol. 500, pp. 232-236.

Rettedal et al., Cultivation-based multiplex phenotyping of human gut microbiota allows targeted recovery of previously uncultured bacteria, Nature Communications 5:4714, p. 1-9, 2014.

Zengler et al., Cultivating the uncultured, PNAS vol. 99, No. 24, 15681-15686, 2002.

Morten OA Sommer, Advancing gut microbiome research using cultivation, Elsevier, Current Opinion in Microbiology 2015, 27:127-132.

Li et al. "RapidAIM: a culture- and metaproteomics based Rapid Assay of Individual Microbiome responses to drugs," Microbiome, 2020, vol. 8, Issue 33, 16 pages.

Laboratorios Ordesa—"Use of Boric Acid in Combination With Probiotics for the Treatment of Vaginal Infections (DOBO)" May 2, 2019—https://clinicaltrials.gov/ct2/show/NCT02860845.

Rodrigues et al., "Vaginal suppositories containing Lactobacillus acidophilus: development and characterization" Drug Development and Industrial Pharmacy, Early Online 1-8, 9 pages, 2014.

Ojala et al., "Comparative genomics of Lactobacillus crispatus suggests novel mechanisms for the competitive exclusion of Gardnerella vaginalis" BMC Genomics 2014, 15:1070.

Abdelmaksoud et al., "Comparison of Lactobacillus crispatus isolates from Lactobacillusdominated vaginal microbiomes with isolates from microbiomes containing bacterial vaginosis-associated bacteria" Microbiology (2016) 162, 466-475.

Yu, Won-Kyu et al., "High Cell Density Cultivation of Bifidobacterium longum Using a Calcium Carbonate-Alginate Beads System" J. Microbiol. Biotechnol. (2002), 12(3), 444-448.

Abraham F. Lash et al., "A Study of Döderlein's Vaginal Bacillus" The Journal of Infectious Diseases, vol. 38, No. 4 (Apr. 1926), pp. 333-340.

(56) References Cited

OTHER PUBLICATIONS

Maria Silvina Juarez Tomas et al., "Viability of vaginal probiotic lactobacilli during refrigerated and frozen storage" Anaerobe 10 (2004) 1-5.
Fabrice Atassi et al., "Lactobacillus strains isolatedfromthevaginalmicrobiotaof healthy women inhibit Prevotella bivia and Gardnerella vaginalis in coculture and cell culture" FEMS Immunol Med Microbiol 48 (2006) 424-432.
Alona Keren-Paz et al., "The formation of microbial 1 exoskeletons is driven by a controlled calcium-concentrating subcellular niche" bioRxiv, 2021.
Belenguer et al., "Two Routes of Metabolic Cross-Feeding between Bifidobacterium adolescentis and Butyrate-Producing Anaerobes from the Human Gut" Applied and Environmental Microbiology, May 2006, p. 3593-3599.
Belzer et al., "Microbial Metabolic Networks at the Mucus Layer Lead to Diet-Independent Butyrate and Vitamin B12 Production by Intestinal Symbionts" Sep./Oct. 2017 vol. 8 Issue 5, e00770-17, 14 pages.
Bunesova et al., "Mucin Cross-Feeding of Infant Bifidobacteria and Eubacterium hallii" Microb Ecol. Springer Science +Business Media, LLC 2017.
Loo Wee Chia et al., "Deciphering the trophic interaction between Akkermansia muciniphila and the butyrogenic gut commensal Anaerostipes caccae using a metatranscriptomic approach" Antonie van Leeuwenhoek (2018) 111:859-873.
Crost et al., "Mechanistic Insights Into the Cross-Feeding of Ruminococcus gnavus and Ruminococcus bromii on Host and Dietary Carbohydrates" Frontiers in Microbiology, Nov. 2018 | vol. 9 | Article 2558.
Kevin D'hoe et al., "Integrated culturing, modeling and transcriptomics uncovers complex interactions and emergent behavior in a three-species synthetic gut community" eLife 2018;7:e37090, 29 pages.
Promi Das et al., "In vitro co-cultures of human gut bacterial species as predicted from co-occurrence network analysis" 2018, PLoS ONE 13(3): e0195161.
Luc De Vuyst et al., "Cross-feeding between bifidobacteria and butyrate-producing colon bacteria explains bifdobacterial competitiveness, butyrate production, and gas production" International Journal of Food Microbiology 149 (2011) 73-80.
Gwen Falony et al., "Cross-Feeding between Bifidobacterium longum BB536 and Acetate-Converting, Butyrate-Producing Colon Bacteria during Growth on Oligofructose" Applied and Environmental Microbiology, Dec. 2006, p. 7835-7841.
Michael A. Fischbach et al., "Eating For Two: How Metabolism Establishes Interspecies Interactions in the Gut" Cell Host & Microbe 10, Oct. 20, 2011 ᵃ2011 Elsevier Inc.
Akshit Goyal et al., "Ecology-guided prediction of cross-feeding interactions in the human gut microbiome" Nature Communications 2021, 10 pages.
Lea B.S. Hansen et al., "A low-gluten diet induces changes in the intestinal microbiome of healthy Danish adults" Nature Communications 2018, 14 pages.
Michael A. Henson et al., "Byproduct Cross Feeding and Community Stability in an In Silico Biofilm Model of the Gut Microbiome" MDPI Processes 2017, 5, 13.
Heejung Kim et al., "Co-Culture with Bifidobacterium catenulatum Improves the Growth, Gut Colonization, and Butyrate Production of Faecalibacterium prausnitzii: In Vitro and In Vivo Studies" Microorganisms 2020, 8, 788.
Nadja Larsen et al., "Potential of Pectins to Beneficially Modulate the Gut Microbiota Depends on Their Structural Properties" Frontiers in Microbiology, Feb. 2019 | vol. 10 | Article 223.
Mireia Lopez-Siles et al., "Cultured Representatives of Two Major Phylogroups of Human Colonic Faecalibacterium prausnitzii Can Utilize Pectin, Uronic Acids, and Host-Derived Substrates for Growth" 2011, Applied and Environmental Microbiology p. 420-428.
Frédéric Moens et al., "Bifidobacterial inulin-type fructan degradation capacity determines cross-feeding interactions between bifidobacteria and Faecalibacterium prausnitzii" International Journal of Food Microbiology 231 (2016) 76-85.
Michael Jakob Pichler et al., "Butyrate producing colonic Clostridiales metabolise human milk oligosaccharides and cross feed on mucin via conserved pathways" 2020, Nature Communications, 15 pages.
Federico E. Rey et al., "Dissecting the in Vivo Metabolic Potential of Two Human Gut Acetogens" The Journal of Biological Chemistry vol. 285, No. 29, pp. 22082-22090, Jul. 16, 2010.
David Rios-Covian et al., "Enhanced butyrate formation by cross-feeding between Faecalibacterium prausnitzii and Bifidobacterium adolescentis" FEMS Microbiology Letters, 362, 2015, fnv176.
David Ríos-Covián et al., "Intestinal Short Chain Fatty Acids and their Link with Diet and Human Health" Frontiers in Microbiology Feb. 2016|vol. 7|Article 185.
Audrey Rivière et al., "Bifidobacteria and Butyrate-Producing Colon Bacteria: Importance and Strategies for Their Stimulation in the Human Gut" Frontiers in Microbiology Jun. 2016| vol. 7 | Article 979.
Hidenori Shimizu et al., "Membrane filter method to study the effects of Lactobacillus acidophilus and Bifidobacterium ongum on fecal microbiota" Microbiol Immunol 2015; 59: 643-652.
Eva C. Soto-Martin et al., "Vitamin Biosynthesis by Human Gut Butyrate-Producing Bacteria and Cross-Feeding in Synthetic Microbial Communities" mBio Jul./Aug. 2020 vol. 11 Issue 4 e00886-20.
Jaeyun Sung et al., "Global metabolic interaction network of the human gut microbiota for context-specific community-scale analysis" Nature Communications, 2017, 12 pages.
Yoshiki Tanaka et al., "Application of a single-colony coculture technique to the isolation of hitherto unculturable gut bacteria" Microbiol Immunol 2015; 59: 63-70.
Jorge F Va' zquez-Castellanos et al., "Design of synthetic microbial consortia for gut microbiota modulation" Current Opinion in Pharmacology 2019, 49:52-59.
Ophelia S Venturelli et al., "Deciphering microbial interactions in synthetic human gut microbiome communities" Molecular Systems Biology 14: e8157 | 2018, 19 pages.
Ophelia S Venturelli et al., Appendix For "Deciphering microbial interactions in synthetic human gut microbiome communities" 21 pages.
Laura Wrzosek et al., "Bacteroides thetaiotaomicron and Faecalibacterium prausnitzii influence the production of mucus glycans and the development of goblet cells in the colonic epithelium of a gnotobiotic model rodent" BMC Biology 2013, 11:61.
Bebe & Bella—V-Bella®-Patented Boric Acid in a Probiotic Blend Vaginal Suppository-supports Intimate Wellness, Maintenance of Vaginal Ph Balance, Sep. 24, 2020, https://bebeandbella.com/product/v-bella-patented-boric-acid-in-aprobiotic-blend-treatment-for-symptoms-of-vaginal-yeast-and-urogenital-infections/.
Biom Probiotics—Boric Acid+Probiotics+ Prebiotics Suppository(10), Accessed, 2022 https://biomprobiotics.com/product/biom-boric-acidprobiotics-prebiotics-vaginal-infectioncontrol-suppository-pack-10/.
Intimate Wellness Shop—Boric Acid and Probiotic Vaginal Suppositories With Applicator, Oct. 1, 2020, https://intimatewellnessshop.com/products/boric-acid-andprobiotic-suppositories.
Heijden et al., "Analysis of bacterial survival after exposure to reactive oxygen species or antibiotics" Elsevier, Data in Brief 7(2016) 894-899.
Aira et al., "New Procedure to Maintain Fecal Microbiota in a Dry Matrix Ready to Encapsulate" Frontiers in Cellular and Infection Microbiology, Jun. 2022 | vol. 12 | Article 899257, 9 pages.
Firrman, Jenni et al., "Applying Advanced In Vitro Culturing Technology to Study the Human Gut Microbiotia" Journal of Visualized Experiments, 2019, vol. 144, e59054, pp. 1-12.
Takagi, Risa et al., "A Single-Batch Fermentation System to Simulate Human Colonic Microbiota for High-Throughput Evaluation of Prebiotics" PLOS ONE, 2016, pp. 1-16.
Grimaldi, Roberta et al., "Fermentation properties and potential prebiotic activity of Bimuno® galacto-oligosaccharide (65% galacto-oligosaccharide content) on in vitro gut microbiota parameters" British Journal of Nutrition, 2016, vol. 116, pp. 480-486.

(56) References Cited

OTHER PUBLICATIONS

Medina, Daniel et al., "Simulation and modeling of dietary changes in the infant gut microbiome" FEMS Microbiology Ecology, 2018, 94, pp. 1-11.
Van den Abbeele, Pieter et al., "A Comparison of the In Vitro Effects of 2'Fucosyllactose and Lactose on the Composition and Activity of Gut Microbiota from Infants and Toddlers" Nutrients, 2021, 13, 726, pp. 1-22.
Sivieri, Katia et al., "Prebiotic Effect of Fructooligosaccharide in the Simulator of the Human Intestinal Microbial Ecosystem (SHIMER Model)" Journal of Medicinal Food, 2013, 1-8.
O'Donnell, Michelle M. et al., "The Use of a Mini-Bioreactor Fermentation System as a Reproducible, High-Throughput ex vivo Batch Model of the Distal Colon" Frontiers in Microbiology, 2018, vol. 9, Article 1844, pp. 1-9.
Tsitko, Irina et al., "A Small In Vitro Fermentation Model for Screening the Gut Microbiota Effects of Different Fiber Preparations" International Journal of Molecular Sciences, 2019, 20, 1925, pp. 1-16.
Mabwi, Humphrey A. et al., "Synthetic gut microbiome: Advances and challenges" Computational and Structural Biotechnology Journal, 2021, 19, pp. 363-371.
Ceppa, Florencia Andrea et al., "Human Gut-Microbiota Interaction in Neurodegenerative Disorders and Current Engineered Tools for Its Modeling" Frontiers in Cellular and Infection Microbiology, 2020, vol. 10, Article 297, pp. 1-18.
Sardelli, Lorenzo et al., "Technological tools and strategies for culturing human gut microbiota in engineered in vitro models" Biotechnology Bioengineering, 2021, 118, pp. 2886-2905.
Yousi, Fu et al., "Evaluation of the effects of four media on human intestinal microbiota culture in vitro" AMB Express, 2019, 9:69, pp. 1-10.
Jalili-Firoozinezhad, Sasan et al., "A complex human gut microbiome cultured in an anaerobic intestine-on-a-chip" Nat Biomed Eng., 2019, 3(7): pp. 520-531.
Thakkar, Riya D. et al., "Maize Bran Particle Size Governs the Community Composition and Metabolic Output of Human Gut Microbiota in in vitro Fermentations" Frontier in Microbiology, 2020, vol. 11, Article 1009, pp. 1-13.
Cremer, Jonas et al., "Effect of flow and peristaltic mixing on bacterial growth in a gut-like channel" PNAS, 2016, vol. 113, No. 41, pp. 1-6.
Li, Leyuan et al., "An in vitro model maintaining taxon-specific functional activities of the gut microbiome" Nature Communications, 2019, pp. 1-11.
Kim, Hyun Jung et al., "Contributions of microbiome and mechanical deformation to intestinal bacterial overgrowth and inflammation in a human gut-on-a-chip" PNAS, 2015, E7-E15.
Li, Leyuan et al., "Evaluating in vitro culture medium of gut microbiome with orthogonal experimental design and metaproteomics approach" Journal of Proteome Research, 2017, pp. 1-26.
Javdan, Bahar et al., "Personalized Mapping of Drug Metabolism by the Human Gut Microbiome" Cell Press, 2020, 181, 1661-1679.
Biagini, Francesco et al., "A novel 3D in vitro model of the human gut microbiota" Scientific Reports, 2020, 10:21499, pp. 1-12.
Gottschick et al., "Screening of Compounds against Gardnerella vaginalis Biofilms", Plos One, 2016, 11.4. p. 2. DOI:10.1371/journal.pone.0154086.
Glushanova N.A., et al., "Bacterial Biofilms in Human Infectious Pathology" Medicine in Kuzbass, 2015, Issue 2, pp. 30-35.
Grossart et al., Bacterial Colonization of Particles: Growth and Interactions, Applied and Environmental Microbiology, Jun. 2003, p. 3500-3509, vol. 69, No. 6, 2003. DOI: 10.1128/AEM.69.6.3500-3509.2003.
Jorup-Rönström C, Håkanson A, Persson A, Midtvedt T, and Norin E. Feces culture successful therapy in Clostridium difficile diarrhea. Lakartidningen. 2006; PMID: 17153868.
Furet et al., "Comparative assessment of human and farm animal faecal microbiota using real-time quantitative PCR" FEMS Microbiol Ecol 68 (2009) 351-362. DOI:10.1111/j.1574-6941.2009.00671.x.
Nanasombat S, and Sriwong N. Improving viability of freeze-dried lactic acid bacteria using lyoprotectants in combination with osmotic and cold adaptation. KMITL Science and Technology Journal. 2007 7(S1):61-69.
Cody W L, Wilson J W, Hendrixson D R, McIver K S, Hagman K E, Ott C M, Nickerson C A, and Schurr M J. Skim milk enhances the preservation of thawed −80° C. bacterial stocks. J Microbiol Methods. 2008 75(1):135-138. doi:10.1016/j.mimet.2008.05.006.
Kurtmann L, Carlsen C U, Risbo J, and Skibsted L H. Storage stability of freeze-dried Ladobacillus acidophilus (La-5) in relation to water activity and presence of oxygen and ascorbate. 2009 58(2):175-180. doi:10.1016/j.cryobiol.2008.12.001.
Guérin-Danan C. Storage Of Intestinal Bacteria In Samples Frozen With Glycerol. Microbial Ecology in Health and Disease. 1999 11(3): 180-182; https://doi.org/10.1080/089106099435772.
Talwalkar A and Kailasapathy K. The role of oxygen in the viability of probiotic bacteria with reference to *L. acidophilus* and *Bifidobacterium* spp. Curr. Issues Intest. Microbiol. 2004 5:1-8.
Wasfy M, Oyofo B, Elgindy A, and Churilla A. Comparison of Preservation Media for Storage of Stool Samples. Journal of Clinical Microbiology. 1995 33(8):2176-2178.
Lund-Tonnesen et al., "Clostridium difficile-associated diarrhea treated with homologous faeces" Tidsskr Nor Lageforen 118 (1998). PMID: 9531822.
Bakken "Fecal bacteriotherapy for recurrent Clostridium difficile infedion" Anaerobe 15 (2009); doi:10.1016/j.anaerobe.2009.09.007.
Schwan et al., "Relapsing Clostridium difficile Enterocolitis Cured by Rectal Infusion of Normal Faeces". Scand J Infect Dis 16: 21 1-215, 1984. https://doi.org/10.3109/00365548409087145.
Alonso, Virginia Robles, et al., "Linking the gut microbiota to human health", British Journal of Nutrition (2013), 109, S21-S26, Digestive System Research Unit, University Hospital Vall d'Hebron, Ciberehd, Passeig Vall d'Hebron 119-129, 08035 Barcelona, Spain, doi: 10.1017/S0007114512005235.
Costello, Elizabeth K., et al., "Bacterial Community Variation in Human Body Habitats Across Space and Time", NIH Public Access, Author Manuscript, Science. Dec. 18, 2009; 326(5960): 1694-1697, doi: 10.1126/science.1177486.
Dave et al., "Effect of Cysteine on the Viability of Yoghurt and Probiotic Bateria in Yoghurts Made with Commercial Starter Cultures" International Dairy Journal 7 (1997) 537-545.

\* cited by examiner

*Lactobacillus plantarum* biofilm on various matrices

Organic matrices

Pomegranate

Passion fruit

Inorganic matrices

White clay

Sand

Bentonite clay

*Lactobacillus plantarum* biofilm on various matrices
Synthetic matrices

Avicel

DCP

Solka fibers

*Acetobacter pomorum* biofilm on various matrices

Organic

Pomegranate

Passion fruit

Sand

*Pseudomonas spp.* biofilm on various matrices

Organic matrices

Passion fruit

Pomegranate

SYSTEMS AND METHODS FOR GROWING A BIOFILM OF PROBIOTIC BACTERIA ON SOLID PARTICLES FOR COLONIZATION OF BACTERIA IN THE GUT

CROSS REFERENCE TO RELATED APPLICATIONS

This application is a Continuation of U.S. application Ser. No. 15/572,972, filed on Nov. 9, 2017, which is a national phase of PCT Patent Application No. PCT/IB2016/000933 having International filing date of May 9, 2016, which claims the benefit of priority to U.S. Provisional Patent Application Ser. No. 62/159,846, filed on May 11, 2015, and U.S. Provisional Patent Application Ser. No. 62/159,849, filed on May 11, 2015, the entire contents of which are hereby incorporated by reference in their entirety.

FIELD OF THE INVENTION

The present invention relates to system and method for growing and encapsulating at least one strain of bacteria in a biofilm form, configured for pH dependent targeted release of the bacterial biofilm in the gastrointestinal tract.

SUMMARY

In one embodiment, the present invention provides a method,
  wherein the method forms a biofilm,
  wherein the biofilm comprises a population of at least one bacterial strain attached to particles,
  wherein the biofilm is configured to colonize a gut of a subject in need thereof for at least five days, when ingested by the subject, the method comprising:
  a. obtaining a population comprising at least one strain of bacteria;
  b. inoculating a growth medium containing particles with the population comprising at least one strain of bacteria;
  c. incubating the particles with the population comprising at least one bacterial strain for a time sufficient for the population of at least one strain of bacteria to attach to the particles; and
  d. culturing the population comprising at least one strain of bacteria attached to the particles in a growth medium, for a time sufficient to form a biofilm.

In one embodiment, the biofilm comprising a population of at least one bacterial strain attached to particles is encapsulated with a compound configured to release the at least one bacterial strain at a pH found in the intestine of the animal.

In one embodiment, the compound configured to release the at least one bacterial strain at a pH found in the intestine of the animal is alginate.

In one embodiment, the population of at least one strain of bacteria attached to the particles is cultured in the growth medium under flow conditions.

In one embodiment, the population of at least one strain of bacteria attached to the particles is cultured in the growth medium under static conditions.

In one embodiment, the population of at least one strain of bacteria attached to the particles is first cultured in the growth medium under static conditions, followed by culture in the growth medium under flow conditions.

In one embodiment, the population of at least one strain of bacteria attached to the particles is cultured under anaerobic conditions.

In one embodiment, the population of at least one strain of bacteria attached to the particles is cultured under aerobic conditions.

In one embodiment, the particles are porous, and selected from the group consisting of: seeds, dicalcium phosphate, clay, sand and cellulose.

In one embodiment, the population comprising at least one bacterial strain is derived from gut microflora.

In one embodiment, the population comprising at least one bacterial strain is *Lactobacillus plantarum*.

In one embodiment, the population comprising at least one bacterial strain is *Acetobacter pomorum*.

In one embodiment, the biofilm formed by the method is configured for pH dependent targeted release of the bacterial biofilm in the gastrointestinal tract.

In one embodiment, the biofilm comprises two or more strains of bacteria.

DETAILED DESCRIPTION

Figure 1:
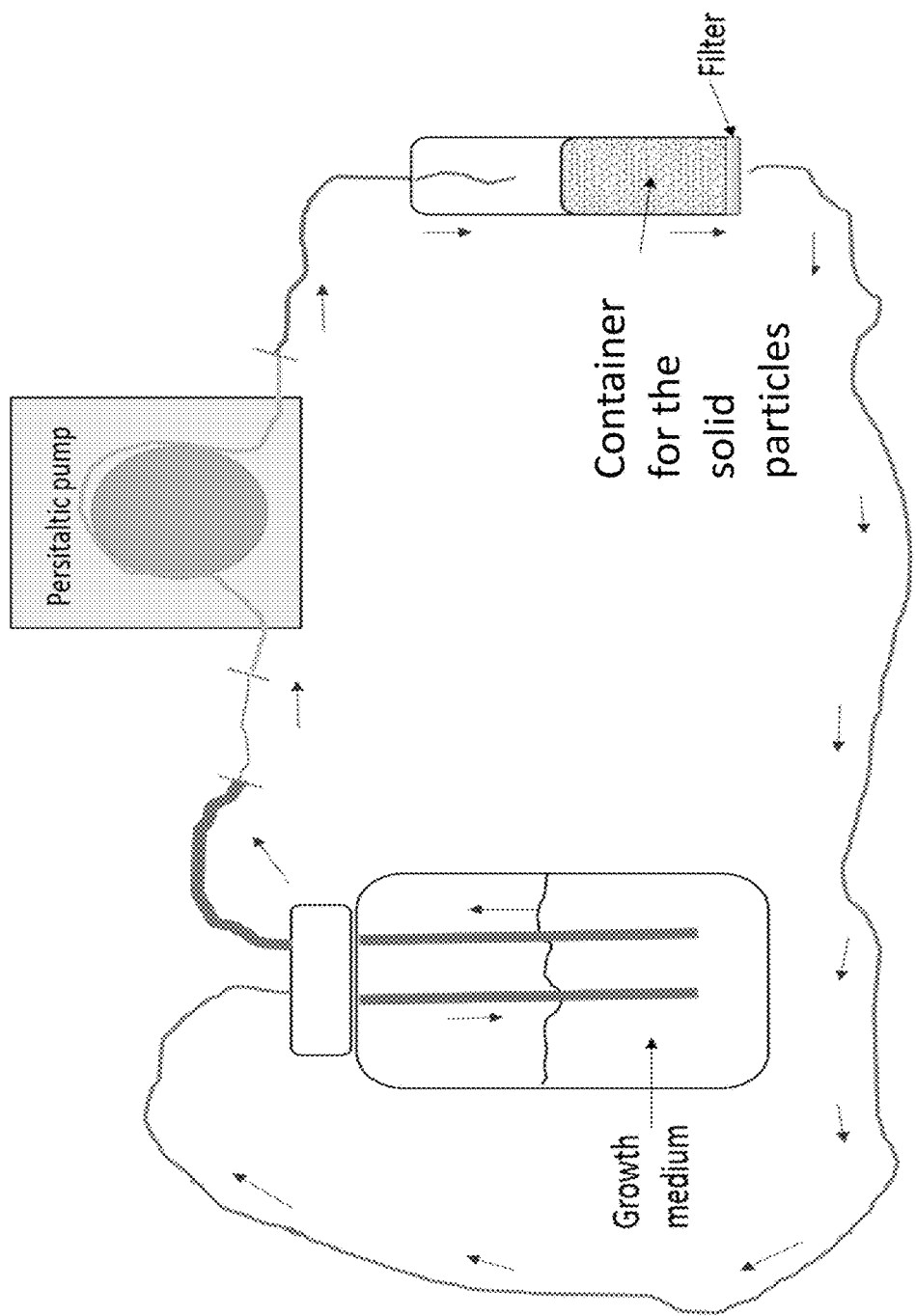
FIG. 1 shows an illustration of an exemplary embodiment of the present invention, showing a flow system used according to the methods according to some embodiments of the present invention.

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the present invention relates to system and method for growing and encapsulating at least one strain of bacteria in a biofilm form, configured for pH dependent targeted release of the bacterial biofilm in the gastrointestinal tract.

In one embodiment, the present invention provides a method,
wherein the method forms a biofilm,
wherein the biofilm comprises a population of at least one bacterial strain attached to particles,
wherein the biofilm is configured to colonize a gut of a subject in need thereof for at least five days, when ingested by the subject, the method comprising:
  a. obtaining a population comprising at least one strain of bacteria;
  b. inoculating a growth medium containing particles with the population comprising at least one strain of bacteria;
  c. incubating the particles with the population comprising at least one bacterial strain for a time sufficient for the population of at least one strain of bacteria to attach to the particles; and
  d. culturing the population comprising at least one strain of bacteria attached to the particles in a growth medium, for a time sufficient to form a biofilm.

In some embodiments, the time sufficient for the population of at least one strain of bacteria to attach to the particles is from 2 hours to 12 hours. In some embodiments, the time sufficient for the population of at least one strain of bacteria to attach to the particles is 2 hours. In some embodiments, the time sufficient for the population of at least one strain of bacteria to attach to the particles is 4 hours. In some embodiments, the time sufficient for the population of at least one strain of bacteria to attach to the particles is 6 hours. In some embodiments, the time sufficient for the population of at least one strain of bacteria to attach to the particles is 8 hours. In some embodiments, the time sufficient for the population of at least one strain of bacteria to attach to the particles is 10 hours. In some embodiments, the time sufficient for the population of at least one strain of bacteria to attach to the particles is 12 hours.

In some embodiments, the time sufficient to form a biofilm is from 12 hours to 48 hours. In some embodiments, the time sufficient to form a biofilm is 12 hours. In some embodiments, the time sufficient to form a biofilm is 14 hours. In some embodiments, the time sufficient to form a biofilm is 16 hours. In some embodiments, the time sufficient to form a biofilm is 18 hours. In some embodiments, the time sufficient to form a biofilm is 20 hours. In some embodiments, the time sufficient to form a biofilm is 22 hours. In some embodiments, the time sufficient to form a biofilm is 24 hours. In some embodiments, the time sufficient to form a biofilm is 26 hours. In some embodiments, the time sufficient to form a biofilm is 28 hours. In some embodiments, the time sufficient to form a biofilm is 30 hours. In some embodiments, the time sufficient to form a biofilm is 32 hours. In some embodiments, the time sufficient to form a biofilm is 34 hours. In some embodiments, the time sufficient to form a biofilm is 36 hours. In some embodiments, the time sufficient to form a biofilm is 38 hours. In some embodiments, the time sufficient to form a biofilm is 40 hours. In some embodiments, the time sufficient to form a biofilm is 42 hours. In some embodiments, the time sufficient to form a biofilm is 44 hours. In some embodiments, the time sufficient to form a biofilm is 46 hours. In some embodiments, the time sufficient to form a biofilm is 48 hours.

In some embodiments, the population of at least one strain of bacteria attached to the particles is cultured in the growth medium under flow conditions. As used herein, the term "flow conditions" refers to the movement of culture medium in relation to bacteria attached to a surface, wherein the movement of the culture medium exerts a shear force on the bacteria.

Without intending to be limited to any particular theory, culturing the population of at least one strain of bacteria attached to the particles under flow conditions creates even gentle shear forces on the growing biofilm and increases the fast creation of the biofilm (e.g., in a shorter period of time compared with typical stationary growth methods). In some embodiments, a flowing system allows for the introduction of fresh culture medium to the growing biofilm, and the removal of bacterial waste.

In some embodiments, the flow conditions comprise a flow rate of 10 ml/hour to 100 ml/hour. In some embodiments, the flow conditions comprise a flow rate of 20 ml/hour. In some embodiments, the flow conditions comprise a flow rate of 30 ml/hour. In some embodiments, the flow conditions comprise a flow rate of 40 ml/hour. In some embodiments, the flow conditions comprise a flow rate of 50 ml/hour. In some embodiments, the flow conditions comprise a flow rate of 60 ml/hour. In some embodiments, the flow conditions comprise a flow rate of 70 ml/hour. In some embodiments, the flow conditions comprise a flow rate of 80 ml/hour. In some embodiments, the flow conditions comprise a flow rate of 90 ml/hour. In some embodiments, the flow conditions comprise a flow rate of 100 ml/hour. In some embodiments, the flow conditions comprise a flow rate of 10 ml/hour.

In some embodiments, the flow conditions comprise shaking the culture of bacteria from 90 to 150 rpm. In some embodiments, the flow conditions comprise shaking the culture of bacteria at 100 rpm. In some embodiments, the flow conditions comprise shaking the culture of bacteria at 110 rpm. In some embodiments, the flow conditions comprise shaking the culture of bacteria at 120 rpm. In some embodiments, the flow conditions comprise shaking the culture of bacteria at 130 rpm. In some embodiments, the flow conditions comprise shaking the culture of bacteria at 140 rpm. In some embodiments, the flow conditions comprise shaking the culture of bacteria at 150 rpm.

In some embodiments, culturing the population of at least one strain of bacteria attached to the particles under flow conditions results in producing a robust and healthy biofilm in a shorter period of time compared with typical methods (e.g., but not limited to, 5, 10, 20, 25, 50% less time). In some embodiments, the resulting biofilm has an increased resilience to harsh conditions when compared with other culturing methods, and is further detailed herein.

Referring to FIG. 1, an illustration of an exemplary embodiment of the present invention, showing a flow system according to some embodiments of the present invention is shown. Referring to FIG. 1, the system includes a container that contains the solid particles for biofilm cultivation, a source of growth medium, tubes that conduct the growth medium in and out of the container, and a pump that moves the medium through the tubes. The fluid outlet from the container can return to the medium reservoir for recycling, or can be drained away. In some embodiments, this flow system can be closed, open, or semi-closed. The clockwise moving arrows in FIG. 1 represent the direction of the flow, and are for illustration purposes only.

In some embodiments, the population of at least one strain of bacteria attached to the particles is cultured in the growth medium under static conditions. As used herein, the term "static conditions" refers to culture conditions where no shear forces exerted on the bacteria.

In some embodiments, the population of at least one strain of bacteria attached to the particles is first cultured in the growth medium under static conditions, followed by culture in the growth medium under flow conditions.

In some embodiments, the population of at least one strain of bacteria attached to the particles is cultured under anaerobic conditions. As used herein, the term "anaerobic conditions" refers to culture conditions comprising the absence of free or bound oxygen.

In some embodiments, the population of at least one strain of bacteria attached to the particles is cultured under aerobic conditions. As used herein, the term "aerobic conditions" refers to culture conditions comprising the presence of free or bound oxygen.

Particles

In some embodiments, the particles are porous, and selected from the group consisting of: seeds, dicalcium phosphate, clay, sand, and cellulose.

In some embodiments, the seeds are selected from the group consisting of: pomegranate seeds, and passion fruit seeds. In some embodiments, the seeds are crushed.

In some embodiments, the cellulose particles comprise cellulose sold under the tradename AVICEL®. In some embodiments, the cellulose particles comprise cellulose sold under the tradename SOLKA®.

In some embodiments, a plurality of particles is used in the method to form a biofilm according to some embodiments of the present invention. In some embodiments, the particles range from 5 microns to 1 cm in diameter. In some embodiments, the particles are 5 microns in diameter. In some embodiments, the particles are 10 microns in diameter. In some embodiments, the particles are 15 microns in diameter. In some embodiments, the particles are 20 microns in diameter. In some embodiments, the particles are 30 microns in diameter. In some embodiments, the particles are 40 microns in diameter. In some embodiments, the particles are 50 microns in diameter. In some embodiments, the particles are 60 microns in diameter. In some embodiments, the particles are 70 microns in diameter. In some embodiments, the particles are 80 microns in diameter. In some embodiments, the particles are 90 microns in diameter. In some embodiments, the particles are 100 microns in diameter. In some embodiments, the particles are 200 microns in diameter. In some embodiments, the particles are 300 microns in diameter. In some embodiments, the particles are 400 microns in diameter. In some embodiments, the particles are 500 microns in diameter. In some embodiments, the particles are 600 microns in diameter. In some embodiments, the particles are 700 microns in diameter. In some embodiments, the particles are 800 microns in diameter. In some embodiments, the particles are 900 microns in diameter. In some embodiments, the particles are 1 cm in diameter.

Bacterial Strains

In some embodiments, the population comprising at least one bacterial strain is derived from intestinal flora.

In some embodiments, the population comprising at least one bacterial strain is a probiotic strain. As used herein, the term "probiotic" refers to a bacterial strain that stimulates the growth of microorganisms, especially those with beneficial properties (such as those of the intestinal flora).

In some embodiments, the population comprising at least one bacterial strain is *Lactobacillus plantarum*.

In some embodiments, the population comprising at least one bacterial strain is *Acetobacter pomorum*.

In some embodiments, the biofilm formed by the method is configured for pH dependent targeted release of the bacterial biofilm in the gastrointestinal tract.

In some embodiments, the biofilm comprises two or more strains of bacteria.

Figure 2A:
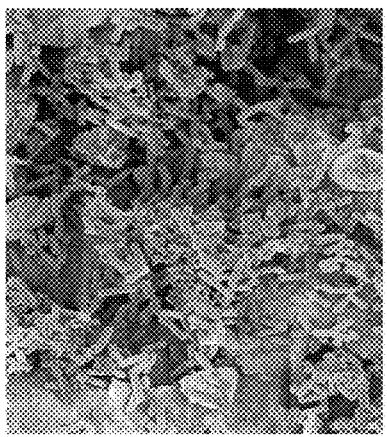
FIG. 2A to 2C show images of some exemplary embodiments of biofilms generated by the methods according to some embodiments of the present invention.
Figure 2A:
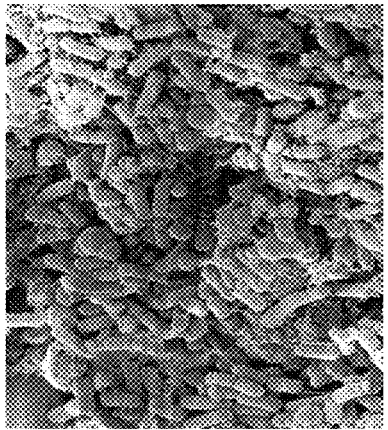
Figure 2A:
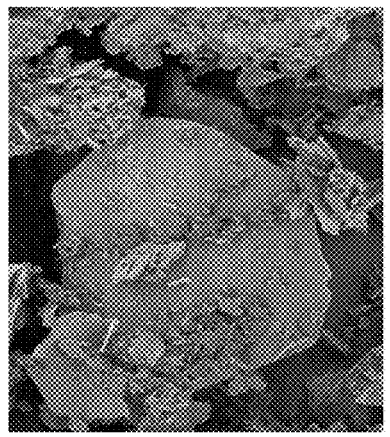
Figure 2A:
Figure 2A:
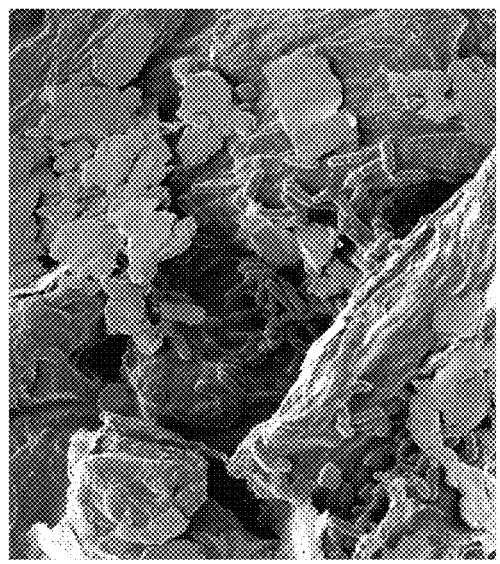
Figure 2A:
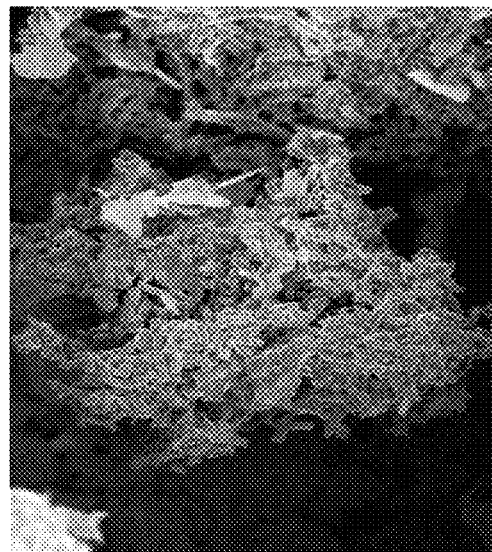
Figure 2A:
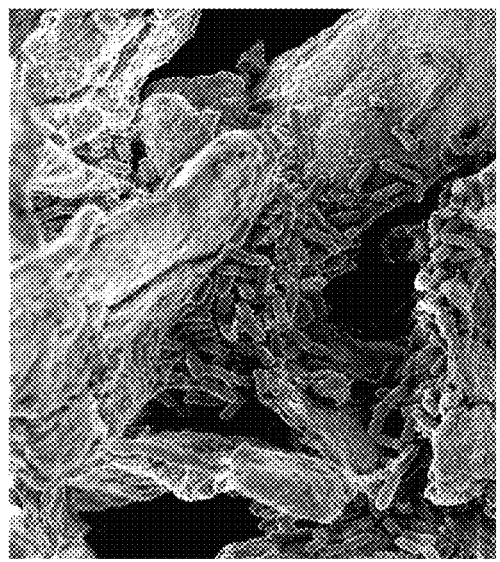

FIG. 2A shows images of some exemplary embodiments of biofilms generated by the methods of the present invention. In some embodiments, several types of solid particles appropriate for growing probiotic bacteria have been tested and the results are shown herein. FIG. 2A shows electron microscope images of *Lactobacillus plantarum* biofilm grown on different solid particles, such as, for example, passion fruit seeds, pomegranate crushed seeds, bentonite clay, sand particles, white clay, SOLKA fibers, dicalcium phosphate (DCP), AVICEL. With the exception of white clay, bacteria grow on all particle types.

Figure 2B:
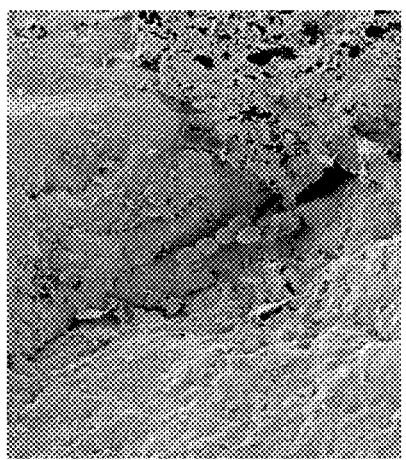
Figure 2B:
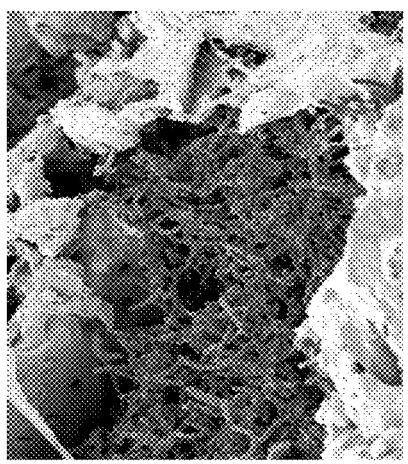
Figure 2B:
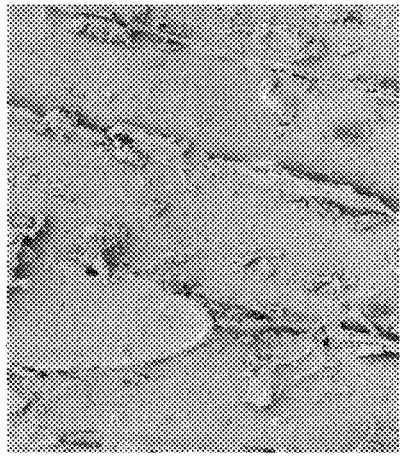
Figure 2C:
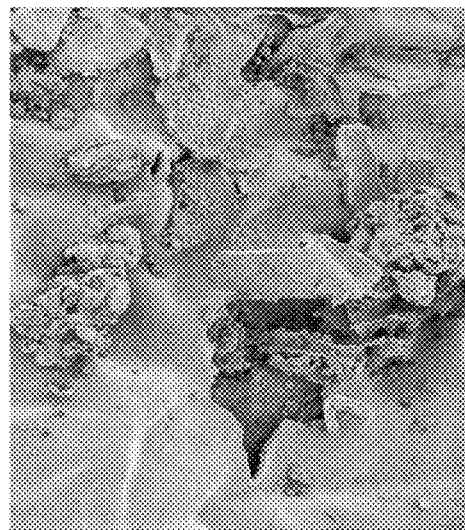
Figure 2C:
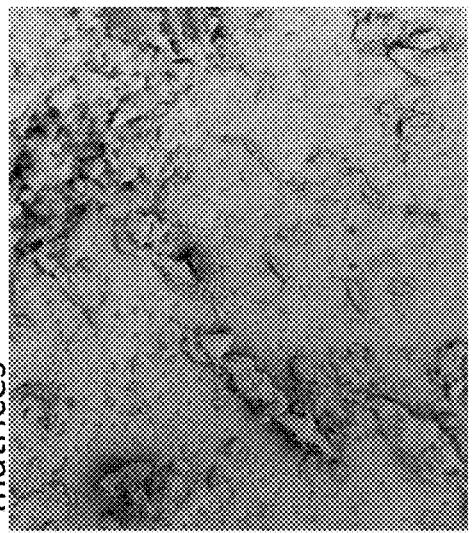

FIG. 2B shows images of some exemplary embodiments of biofilms generated by the methods of the present invention, showing the biofilm growth of *Acetobacter pomorum* on passion fruit crushed seeds, pomegranate crushed seeds, and sand. *Acetobacter pomorum* grew and formed a biofilm on pomegranate seeds. However, very little growth on sand was observed. *Acetobacter pomorum* did not grow on passion fruit seeds. Other bacteria species tested, for example *Pseudomonas* spp, did not grow on the solid particles tested, as shown in FIG. 2C.

Without being bound by theory, different particles provide distinguishable microenvironments for the bacteria to grow on, such as pore size, roughness of the surface, nutrients available in the particles, viscosity, surface charge, etc., which may influence the ability of various bacteria to attach and grow on various kinds of particles.

In some embodiments of the methods of the present invention, the method
generates a biofilm containing at least two strains of probiotic bacteria (e.g., but not limited to, 2, 3, 4, 5, 6, 7, 8, 9, 10, etc.), where the biofilm is generated using a combination of at least two different particles (e.g., but not limited to, passion fruit seeds, pomegranate crushed seeds, etc.). In some embodiments, for creating such combinations, the growth conditions (and, e.g., but not limited to types of particle(s)) are selected according to the strain(s) for use in generating a biofilm. In an exemplary embodiment, if two bacterial strains will eventually be combined to generate a biofilm, each of the bacterial strains will be grown using the particle best suited for the growth of each strain. In some embodiments, when two or more bacterial strains are grown separately, the bacterial strains are combined during the encapsulation process.

Treatment

In some embodiments, a biofilm is administered to an animal in need thereof, to colonize the gut of the animal with the biofilm.

In some embodiments, the biofilm comprising a population of at least one bacterial strain attached to particles is encapsulated with a compound configured to release the at least one bacterial strain at a pH found in the intestine of the animal.

In some embodiments, the compound configured to release the at least one bacterial strain at a pH found in the intestine of the animal is alginate.

In some embodiments, the pH found in the intestine of the animal is pH 8.

In some embodiments, the biofilm is administered to an animal in need thereof in an amount sufficient to colonize the gut. In some embodiments, colonization is confirmed by the presence of the at least one population of bacteria being present in the feces of the animal for at least 5 days post administration.

In some embodiments, the colonized bacteria derived from the biofilm can inhabit the gut of a mammal for at least one week (e.g., but not limited to, 2, 3, 4, 5, 6, 7, 8, 9, 10, etc. weeks). In some embodiments, the colonized bacteria derived from the biofilm are sustainable within a mammalian gut, i.e., do not die off after 3 days.

In some embodiments, the amount sufficient to colonize the gut is $2\times10^4$ to $2\times10^9$ bacteria per day, for 1 to 5 days. In some embodiments, the amount sufficient to colonize the gut is $2\times10^4$ to $2\times10^6$ bacteria per day, for 1 to 5 days.

In some embodiments, the amount sufficient to colonize the gut is $2\times10^4$ bacteria per day, for 5 days. In some embodiments, the amount sufficient to colonize the gut is $2\times10^5$ bacteria per day, for 5 days. In some embodiments, the amount sufficient to colonize the gut is $2\times10^6$ bacteria per day, for 5 days. In some embodiments, the amount sufficient to colonize the gut is $2\times10^7$ bacteria per day, for 5 days. In some embodiments, the amount sufficient to colonize the gut is $2\times10^8$ bacteria per day, for 5 days. In some embodiments, the amount sufficient to colonize the gut is $2\times10^9$ bacteria per day, for 5 days.

In some embodiments, the amount sufficient to colonize the gut is $2\times10^4$ bacteria per day, for 4 days. In some embodiments, the amount sufficient to colonize the gut is $2\times10^5$ bacteria per day, for 4 days. In some embodiments, the amount sufficient to colonize the gut is $2\times10^6$ bacteria per day, for 4 days. In some embodiments, the amount sufficient to colonize the gut is $2\times10^7$ bacteria per day, for 4 days. In some embodiments, the amount sufficient to colonize the gut is $2\times10^8$ bacteria per day, for 4 days. In some embodiments, the amount sufficient to colonize the gut is $2\times10^9$ bacteria per day, for 4 days.

In some embodiments, the amount sufficient to colonize the gut is $2\times10^4$ bacteria per day, for 3 days. In some embodiments, the amount sufficient to colonize the gut is $2\times10^5$ bacteria per day, for 3 days. In some embodiments, the amount sufficient to colonize the gut is $2\times10^6$ bacteria per day, for 3 days. In some embodiments, the amount sufficient to colonize the gut is $2\times10^7$ bacteria per day, for 3 days. In some embodiments, the amount sufficient to colonize the gut is $2\times10^8$ bacteria per day, for 3 days. In some embodiments, the amount sufficient to colonize the gut is $2\times10^9$ bacteria per day, for 3 days.

In some embodiments, the amount sufficient to colonize the gut is $2\times10^4$ bacteria per day, for 2 days. In some embodiments, the amount sufficient to colonize the gut is $2\times10^5$ bacteria per day, for 2 days. In some embodiments, the amount sufficient to colonize the gut is $2\times10^6$ bacteria per day, for 2 days. In some embodiments, the amount sufficient to colonize the gut is $2\times10^7$ bacteria per day, for 2 days. In some embodiments, the amount sufficient to colonize the gut is $2\times10^8$ bacteria per day, for 2 days. In some embodiments, the amount sufficient to colonize the gut is $2\times10^9$ bacteria per day, for 2 days.

In some embodiments, the amount sufficient to colonize the gut is $2\times10^4$ bacteria per day, for 1 day. In some embodiments, the amount sufficient to colonize the gut is $2\times10^5$ bacteria per day, for 1 day. In some embodiments, the amount sufficient to colonize the gut is $23\times10^6$ bacteria per day, for 1 day. In some embodiments, the amount sufficient to colonize the gut is $2\times10^7$ bacteria per day, for 1 day. In some embodiments, the amount sufficient to colonize the gut is $2\times10^8$ bacteria per day, for 1 day. In some embodiments, the amount sufficient to colonize the gut is $2\times10^9$ bacteria per day, for 1 day.

In some embodiments, the amount sufficient is administered on a single particle. Alternatively, the amount sufficient is administered on a plurality of particles.

In some embodiments, the amount sufficient is mixed with food, and ingested.

In some embodiments, the biofilm is administered to the animal immediately after the biofilm is cultured. Alternatively, the biofilm may be stored, prior to administration. The biofilm may be stored frozen, or, alternatively, in a lyophilized form.

Reference is now made to the following examples, which together with the above descriptions illustrate some embodiments of the invention in a non-limiting fashion.

EXAMPLES

Example 1

Acidity Tolerance of a Biofilm According to Some Embodiments of the Present Invention The resilience of the biofilm grown on solid particles in the flowing system as described above was tested. Specifically, the first parameter tested was acidity tolerance, and the results are shown in FIG. 3.

An overnight culture of *L. plantarum* was inoculated in pomegranate matrix soaked in 25% MRS medium (to encourage biofilm formation, starvation conditions (i.e. less than a 100% concentration of growth medium) were used) in the matrix container and left still for 2.5 hours (i.e., no mixing), and then the flow system was initiated. Medium was moved from the medium reservoir to the matrix container using a peristaltic pump at a speed of 12 ml/hour for a duration of 5 days. The medium was not recycled. Fresh medium entered the culture and the outlet drained away the used media. As a control, bacteria grown planktonically (i.e., not attached to a particle) were used, resulting in a lack of biofilm forming. For the planktonic control, 4-5 colonies of *L. plantarum* were inoculated in 6 ml of 100% MRS broth and left still in incubator at 37° C. overnight.

To test acidity tolerance, a series of vials with PBS adjusted to increasing pH using HCl (stock solution 0.5M) prepared in advance to create pH 1, 2, 3, and 2 grams of the particles having a biofilm was transferred into the vials and incubated for 1 hr. The bacteria were then washed in PBS and 5 microliters were plated as shown in FIG. 3.

Figure 3:
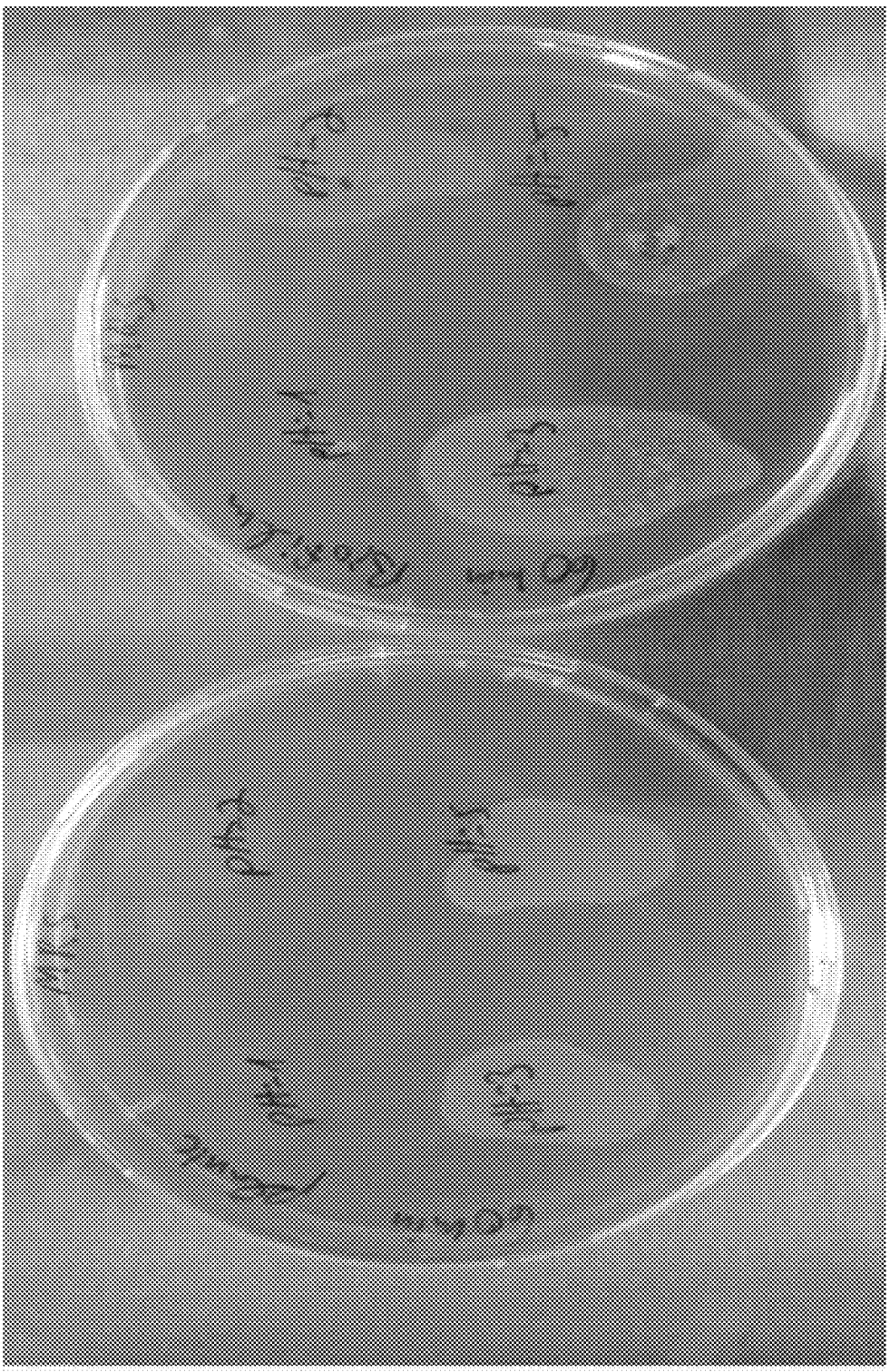
FIG. 3 shows the acidity tolerance of a biofilm according to some embodiments of the present invention.

For the planktonic control, 100μl from the overnight culture were taken into the pH vials and incubated for 1 hr, the bacteria were then washed in PBS and 5 microliters were plated as shown in FIG. 3. As shown in FIG. 3, the biofilm bacteria show a greater resilience to acidity as they survived well pH 2, while the planktonic bacteria did not survive.

Without intending to be limited to any particular theory, the pH in the stomach is about pH 2. Thus, upon administration of the biofilm to a subject, the biofilm will survive the subject's stomach environment (i.e., pH of 2) and colonize the subject.

Example 2

Acidity Tolerance of Another Biofilm According to Some Embodiments of the Present Invention A second set of experiments were conducted and demonstrate bacterial resilience to acidity (i.e., in the form of a biofilm) is described in FIG. 4 and shown in Tables 1 and 2 below.

An overnight culture of *L. plantarum* was inoculated into 7grams of pomegranate (POM) seed particles soaked in 25% MRS medium (starvation conditions), and left still for 2.5 hours. Next, the flowing system was conducted for 5 days, using a peristaltic pump that moved the medium at max speed (about 380 ml/hour). In this experiment, the medium was recycled, to compare to the non flowing/stationary control. For planktonic control, 4 colonies of *L. plantarum* were inoculated in 6 ml of 100% MRS broth and left in incubator 37° C. overnight +5 hours. Results are shown in Tables 1 and 2.

TABLE 1

Cell Growth

| pH | Planktonic (cells/ml) | | Biofilm flow (cells/1 gr matrix) | |
|---|---|---|---|---|
| 1.5 | $2 * 10^4$ | $2.3 * 10^4$ | — | — |
| 2 | $5.6 * 10^5$ | $3.3 * 10^5$ | $5 * 10^8$ | $4 * 10^8$ |
| 2.5 | $3 * 10^6$ | $6.6 * 10^6$ | $4.5 * 10^8$ | $5.6 * 10^8$ |
| 3 | $6.3 * 10^8$ | $6.3 * 10^8$ | $4.3 * 10^8$ | $5.1 * 10^8$ |
| 4 | $6.3 * 10^8$ | $4 * 10^8$ | $10^9$ | $1.3 * 10^9$ |
| 7.4 | $1.1 * 10^9$ | $1.1 * 10^9$ | $3 * 10^8$ | $3.8 * 10^8$ |

TABLE 2

Figure 4:
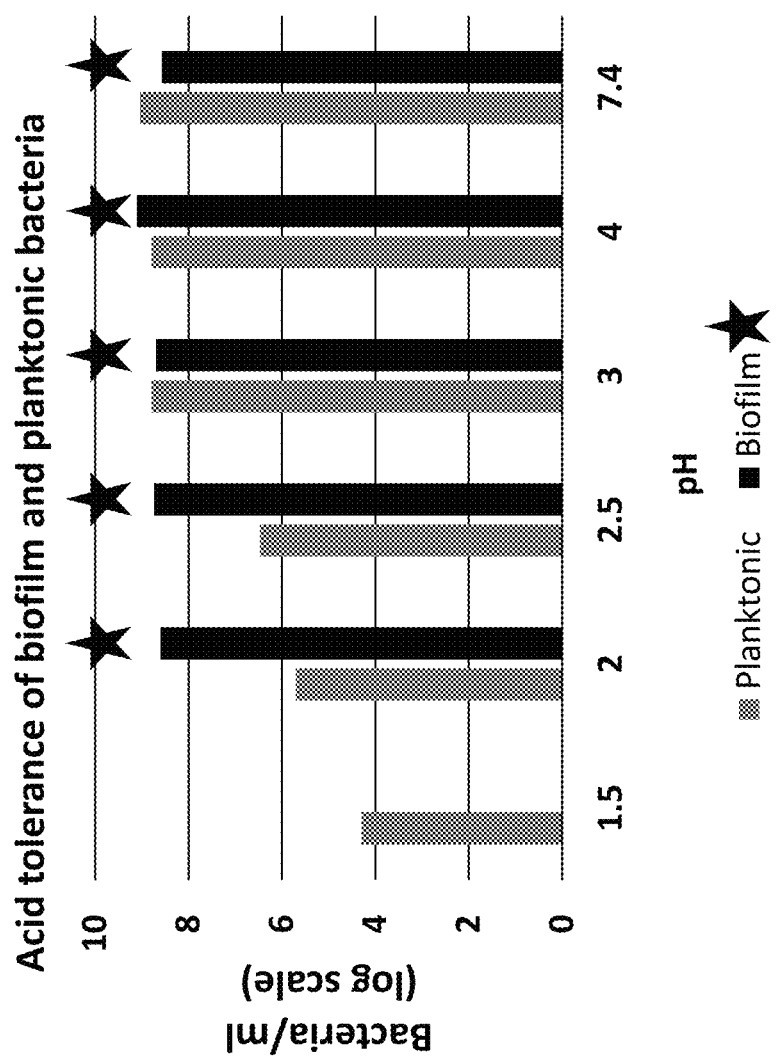
FIG. 4 shows the acidity tolerance of another biofilm according to some embodiments of the present invention.

Data of FIG. 4 (Log of Results)

| pH | Planktonic (cells/ml) | | Biofilm flow (cells/1gr matrix) | |
|---|---|---|---|---|
| 1.5 | 4.3 | 4.36 | — | — |
| 2 | 5.7 | 5.51 | 8.69 | 8.6 |
| 2.5 | 6.47 | 6.81 | 8.65 | 8.74 |
| 3 | 8.79 | 8.79 | 8.63 | 8.7 |
| 4 | 8.79 | 8.6 | 9 | 9.11 |
| 7.4 | 9.04 | 9.04 | 8.47 | 8.57 |

As shown in FIG. 4, the planktonic bacteria showed decreasing survival when exposed to decreasing pH.

Example 3

Figure 5:
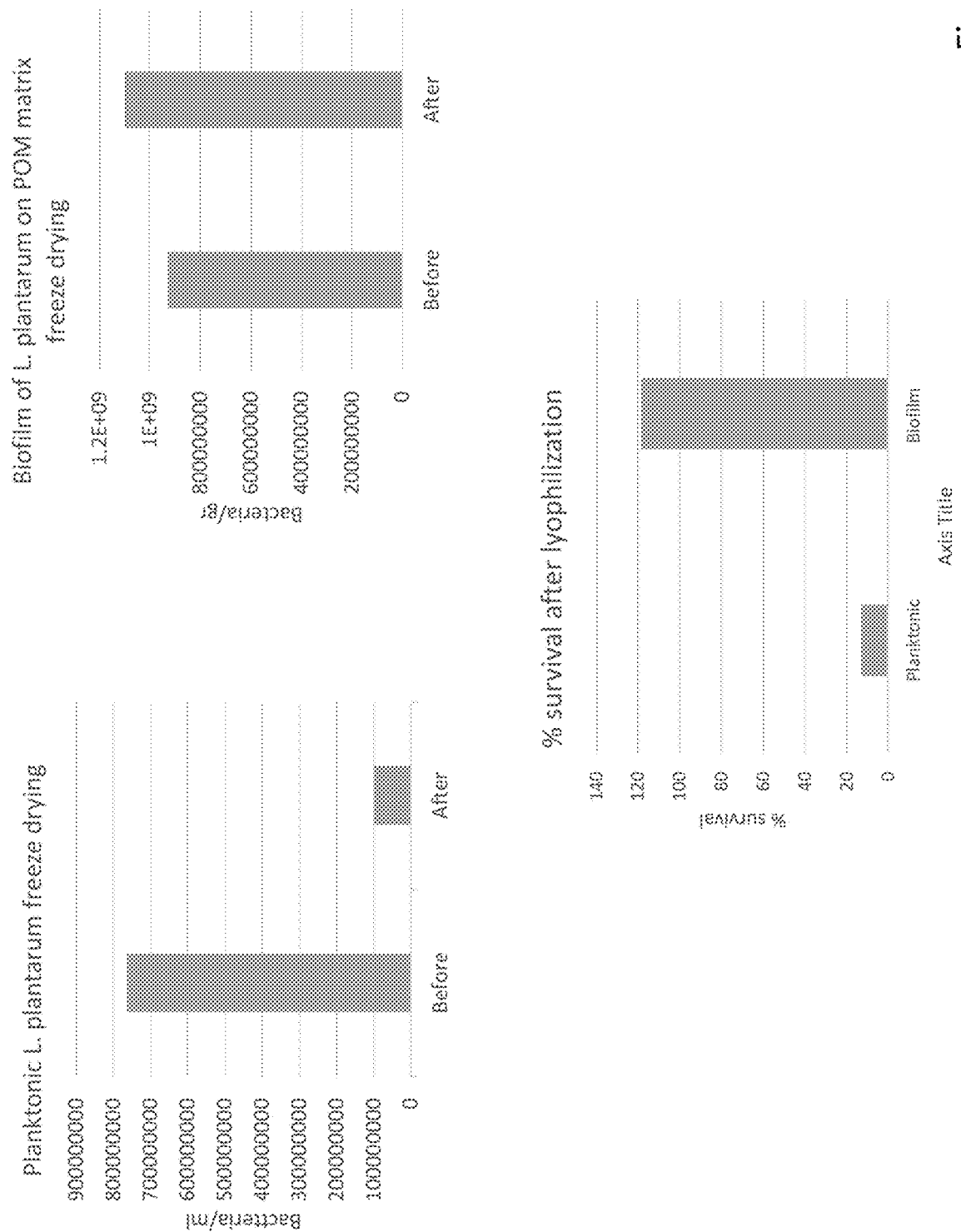
FIG. 5 shows the tolerance of a biofilm according to some embodiments of the present invention to lyophilization.

Reconstitution of a Biofilm According to Some Embodiments of the Present Invention The biofilm grown and entrapped in alginate recovered after drying. *L. plantarum* was grown in 25 ml 100% MRS+2 gr POM for 4 days at room temperature to form biofilms. For planktonic control, *L. plantarum* was grown in 25 ml 100% MRS for 4 days at room temp. One sample of POM+biofilm and control were plated on MRS plates in serial dilutions. Another sample of each was centrifuged briefly, resuspended in 5 ml freeze drying buffer, lyophilized for 24 hours, and suspended in 25 mL MRS. At this stage (after lyophylization but before further growth), samples were plated by serial dilutions. The remainder of the sample was left to grow for 48 additional hours, and plated again. As shown in FIG. 5, bacteria that grew as biofilm on solid particles showed an enhanced resistance and survival to lyophilization (i.e., reconstitution after drying).

Example 4

Acid Tolerance of *E. coli* DH5α Cells

Acid tolerance of *E. coli* strain DH5α was tested under three conditions:
1. Planktonic—*E. coli* grown in 20 ml LB starter in shaker for 5 days at 23° C.
2. Biofilm static—*E. coli* grown in 20 ml LB with 2 gr of different matrixes grown for 5 days in static conditions at 37° C.
3. Biofilm flow—*E. coli* grown in column flow system with DCP for 5 days at room temperature at a speed of approximately 12ml/hour fresh 25% LB. Samples were taken from the top of the column (close to the air surface) and from the bottom of the column.

*E. coli* strain DH5α starter was grown overnight in 37oC shaking. 100μl from the starter was transferred to:
1. 2 gr avicel+20 ml LB—for biofilm static culture.
2. 2 gr Solka fibers+20 ml LB—for biofilm static culture.
3. 3 gr DCP+20 ml LB—for biofilm static culture.
4. 20 ml LB—for planktonic culture.

2 ml of the overnight starter was transferred to 20 ml of LB and inoculated in the column of the flow system. Flow was arrested for 2 hours to let the *E. coli* attach to the DCP. After 2 hours, flow was turned on for 5 days at room temperature.

After 5 days of incubation, a sample from each of the matrixes from the static experiments (DCP, avicel and solka) and a sample from the DCP form the top of the column and DCP form the bottom of the column was taken and inserted into five different Eppendorf tubes ("Eppendorfs"). The samples were gently washed once with PBS.

From each sample, the following amount of matrix was taken into two vials:
1. Static DCP—0.02 gr
2. Static avicel—0.03 gr
3. Static Solka—0.02 gr
4. Flow DPC top—0.03 gr
5. Flow DCP bottom—0.03 gr The content of each Eppendorf was gently washed once with PBSX1. For each pair of eppendorfs (from each sample), 1 ml of PBSX1 (pH=7.4) or 1 ml of PBS (pH=2) was added. The eppendorfs were incubated on their side for 1 hour at room temp. The eppendorfs were then centrifuged at 13,000 rpm for 2 min, the supernatant was discarded. 1 ml of PBSX1 was added to each Eppendorf and the eppendorfs were vortexed at full power for 30 sec to free the bacteria from the matrix.

Handling of the planktonic culture: 1 ml of culture was transferred to an Eppendorf and centrifuged at full speed for 2 min. Supernatant was discarded and 1 ml of PBS was added. 100μl from this was added to:
1. Eppendorf with 1 ml of PBSX1 (pH=7.4)
2. Eppendorf with 1 ml of PBS (pH=2)

The eppendorfs were incubated for 1 hour at room temp on their side, and this incubation was followed by centrifugation at 13,000 rpm for 2 min. 100μl of PBSX1 was added to each Eppendorf.

Viable Counts:

10μl from each eppendorf was transferred to 90μl of PBSX1. Seven 1:10 serial dilutions were conducted. 3μl from each dilution were plated on an LB plate and left in the incubator overnight.

The calculations were as follows to retain bacteria/ml for planktonic or bacteria/gr:

For matrices: Number of colonies X $10^{dilution\ number}$ X333.33X(1/gr taken)

For planktonic: Number of colonies X $10^{dilution\ number}$ X333.3

Figure 6:
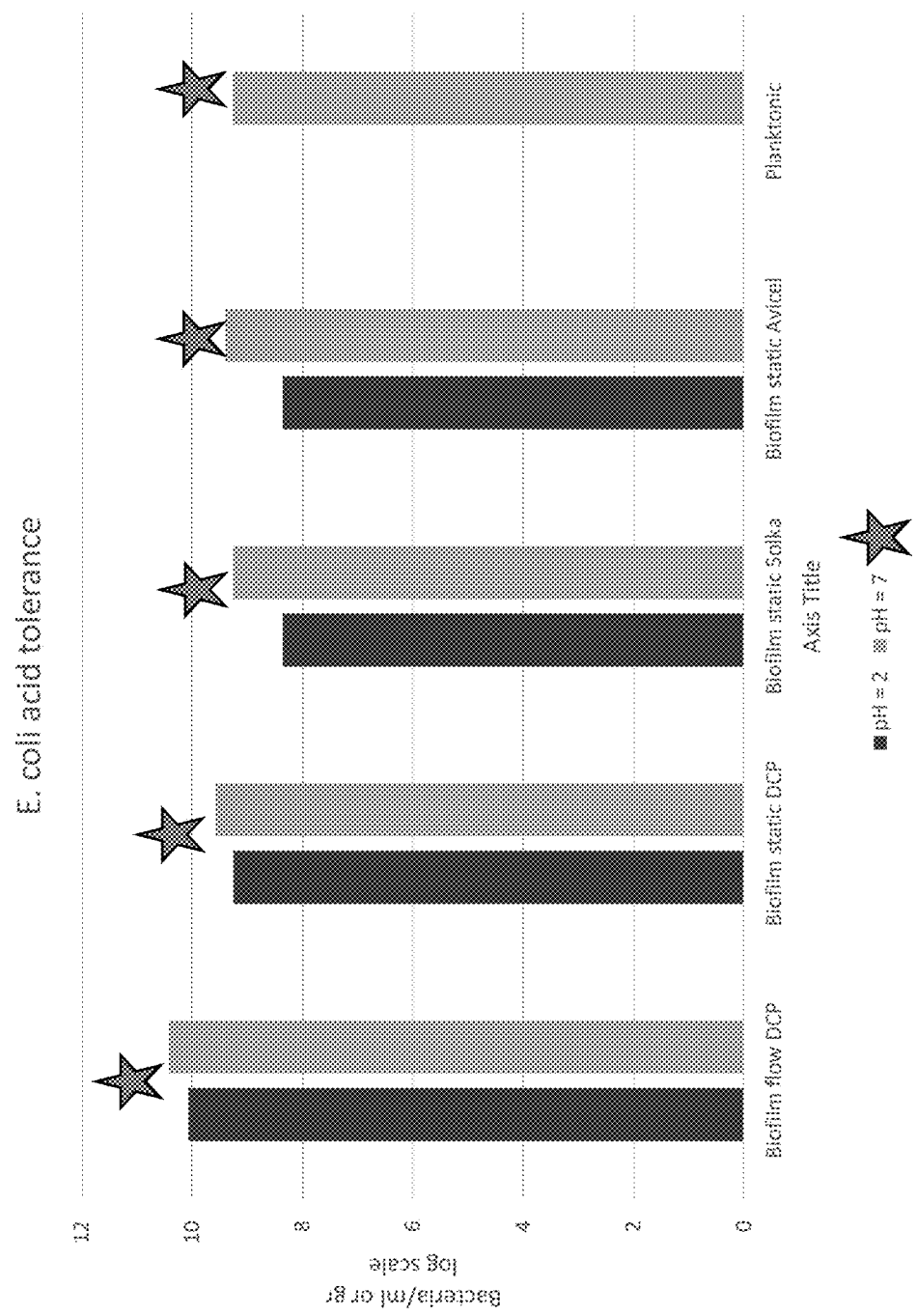
FIG. 6 shows the acidity tolerance of another biofilm according to some embodiments of the present invention.

All materials in this experiment were autoclaved for sterilization. The results as shown in the tables below and in FIG. 6 demonstrate that the biofilm increased the acid tolerance of the bacteria, in the static conditions and exhibited a greater increase in the flow conditions.

TABLE 3

Results (*E. coli* DH5α):

| | pH = 2 | pH = 7 | % survival in pH 2 |
|---|---|---|---|
| Top flow biofilm DCP | $1.2 * 10^{10}$ bacteria/gr | $2.7 * 10^{10}$ bacteria/gr | 44.4% |
| Bottom flow biofilm DCP | $6.6 * 10^{9}$ bacteria/gr | $1.4 * 10^{10}$ bacteria/gr | 47.1% |
| Static biofilm DCP | $1.8 * 10^{9}$ bacteria/gr | $3.8 * 10^{9}$ bacteria/gr | 47.36% |
| Static biofilm Solka | $2.3 * 10^{8}$ bacteria/gr | $1.8 * 10^{9}$ bacteria/gr | 12.7% |
| Static biofilm Avicel | $2.3 * 10^{8}$ bacteria/gr | $2.6 * 10^{9}$ bacteria/gr | 8.8% |
| Planktonic | 0 bacteria/ml | $1.9 * 10^{9}$ bacteria/ml | 0% |

TABLE 4

Log Scale

| | pH = 2 | pH = 7 | % survival in pH 2 |
|---|---|---|---|
| Top flow biofilm DCP | 10.07 | 10.43 | 44.4% |
| Bottom flow biofilm DCP | 9.8 | 10.14 | 47.1% |
| Static biofilm DCP | 9.25 | 9.57 | 47.36% |
| Static biofilm Solka | 8.36 | 9.25 | 12.7% |
| Static biofilm Avicel | 8.36 | 9.41 | 8.8% |
| Planktonic | 0 | 9.27 | 0% |

Example 5

Colonization of Murine Gut Using a Composition According to Some Embodiments of the Present Invention To test whether the bacteria grown as biofilm show enhanced ability to colonize the gut, biofilm was prepared as described above, and the biofilm fed to nude mice. The presence of bacteria in the mouse feces was tested. The results are shown in FIG. 7.

Protocol:
1. 6 germ-free mice
2. *Lactobacillus plantarum* biofilm grown on matrix.
3. Ground food for mice mixed with sterile matrix only (Grind together).
4. Ground food for mice mixed with *L. plantarum* biofilm on matrix (Grind together).
5. Ground food for mice mixed with *L. plantarum* biofilm in alginate beads.
6. Live-dead staining kit (to determine presence of live bacteria).
7. Autoclave matrix for control mice.
8. The mice were divided into 3 groups (2 mice for each group):
   a. Control—mice that are fed food+matrix only.
   b. Biofilm—mice that are fed with food+biofilm on matrix.
   c. Biofilm alginate—mice that are fed with food+biofilm on matrix in alginate beads.
9. Feed mice with corresponding food for 7 days (D1-D7).
10. Sample stool at day 8(D8), day 9 (D9), day 10 (D10), Day 11 (D11), day 12 (D12), day 13 (D13) and day 14 (D14).
11. Check presence of *L. plantarum* in stool samples.
12. Take section from inner intestine to image biofilm of *L. Plantarum* on intestine, and stain for live-dead using a designated staining kit.

Figure 7:
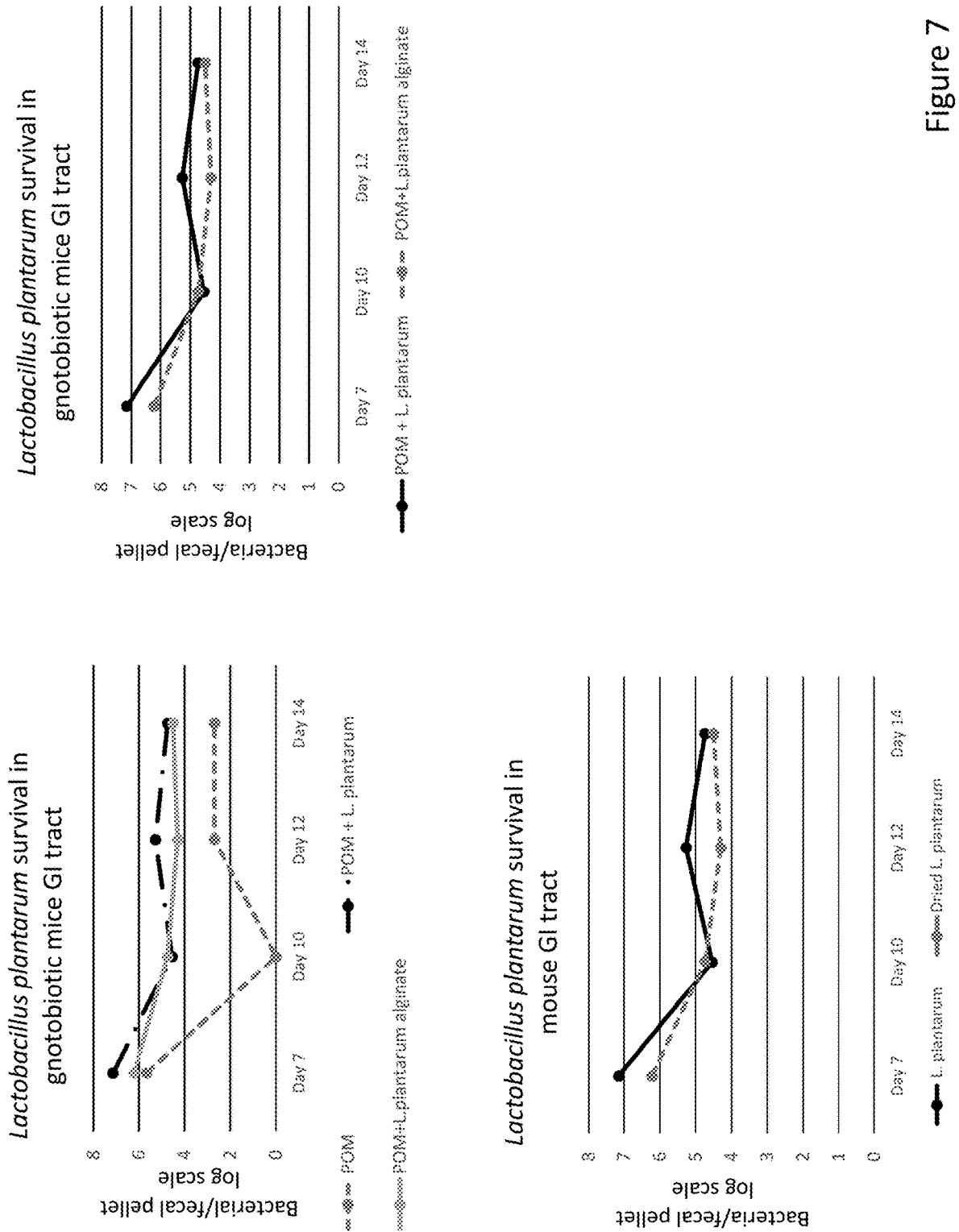
FIG. 7 shows the ability of a biofilm according to some embodiments of the present invention to colonize the gut of an animal model, using the indicated compositions.

FIG. 7 shows that bacteria colonized the gut of the mice. The gut of the mice was colonized with the bacteria derived from the biofilm for more than 3 days, and, in fact, for up to, but not limited to, 14 days.

Figure 8:
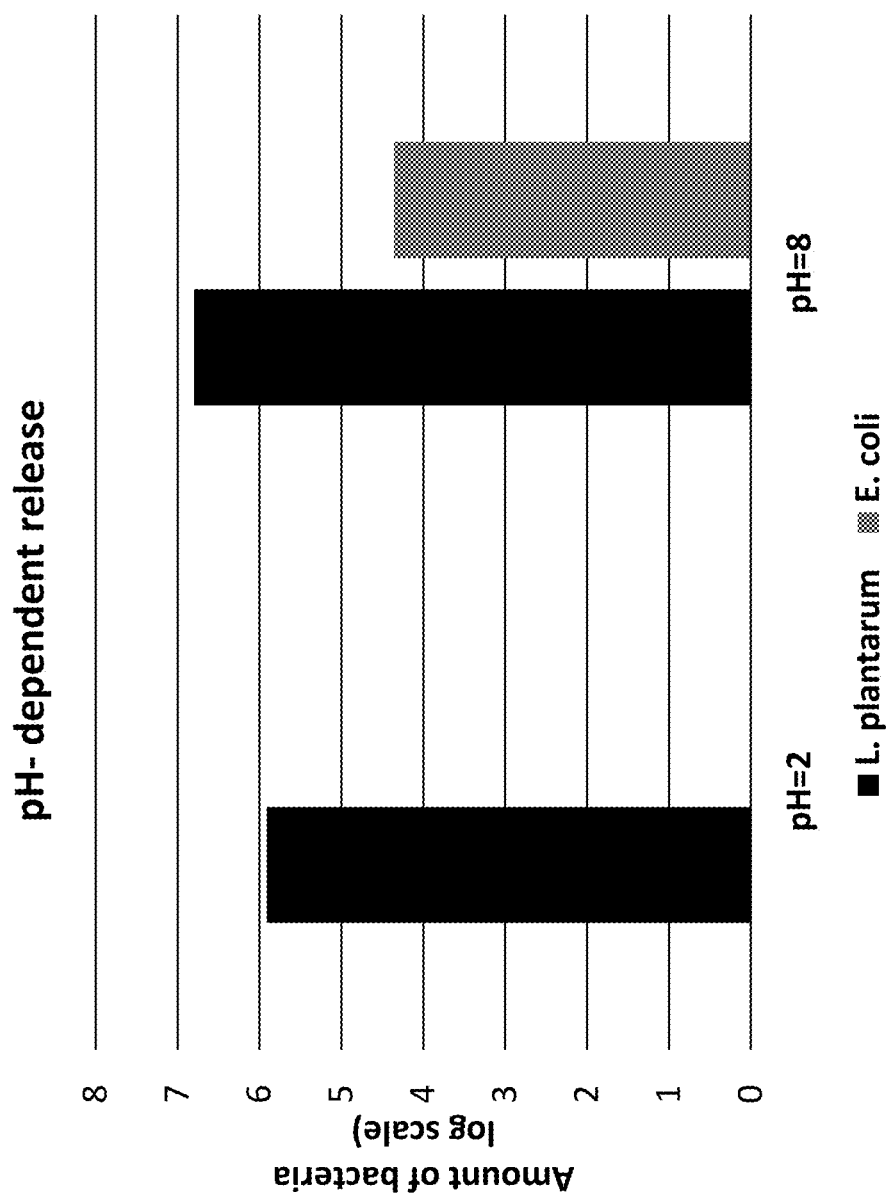
FIG. 8 shows the pH-dependent release of bacteria from biofilms according to some embodiments of the present invention.

Example 6 pH-Dependent Release of Bacteria From a Composition According to Some Embodiments of the Present Invention A biofilm comprising *E. coli* on DCP was encapsulated in alginate by mixing the DCP with the biofilm in 4% alginate and dropping droplets with the material into 2% $CaCl_2$ solution, and a biofilm comprising *L. plantarum* was grown on top of the alginate beads. The resulting compositions were then treated according to Example 1 above. The results are shown in FIG. 8.

Only *Lactobacillus plantarum* was released when the beads were inserted into a solution at pH=2. At pH=8 both *E. coli* and *L. plantarum* were released from the beads.

Example 7

Colonization of Murine Gut Using a Composition Comprising *C. minuta* According to Some Embodiments of the Present Invention A biofilm comprising *C. minuta* on pomegranate seeds was given to SPF mice once at a concentration of $2*10^7$ bacteria at day 1 of the experiment mixed with the food. Feces were checked at day 1 (before probiotic treatment), 2, 4, 7, 11 and 15 for the % of *C. minuta* in the feces.

The animals were treated as follows (three mice per treatment group):
1. Control—Food only (6 gr).
2. Control—Food (3 gr) mixed with pomegranate grains (3 gr) only
3. Experiment—Food (3 gr) mixed with *C. minuta* biofilm on pomegranate grains (3 gr).

Figure 9:
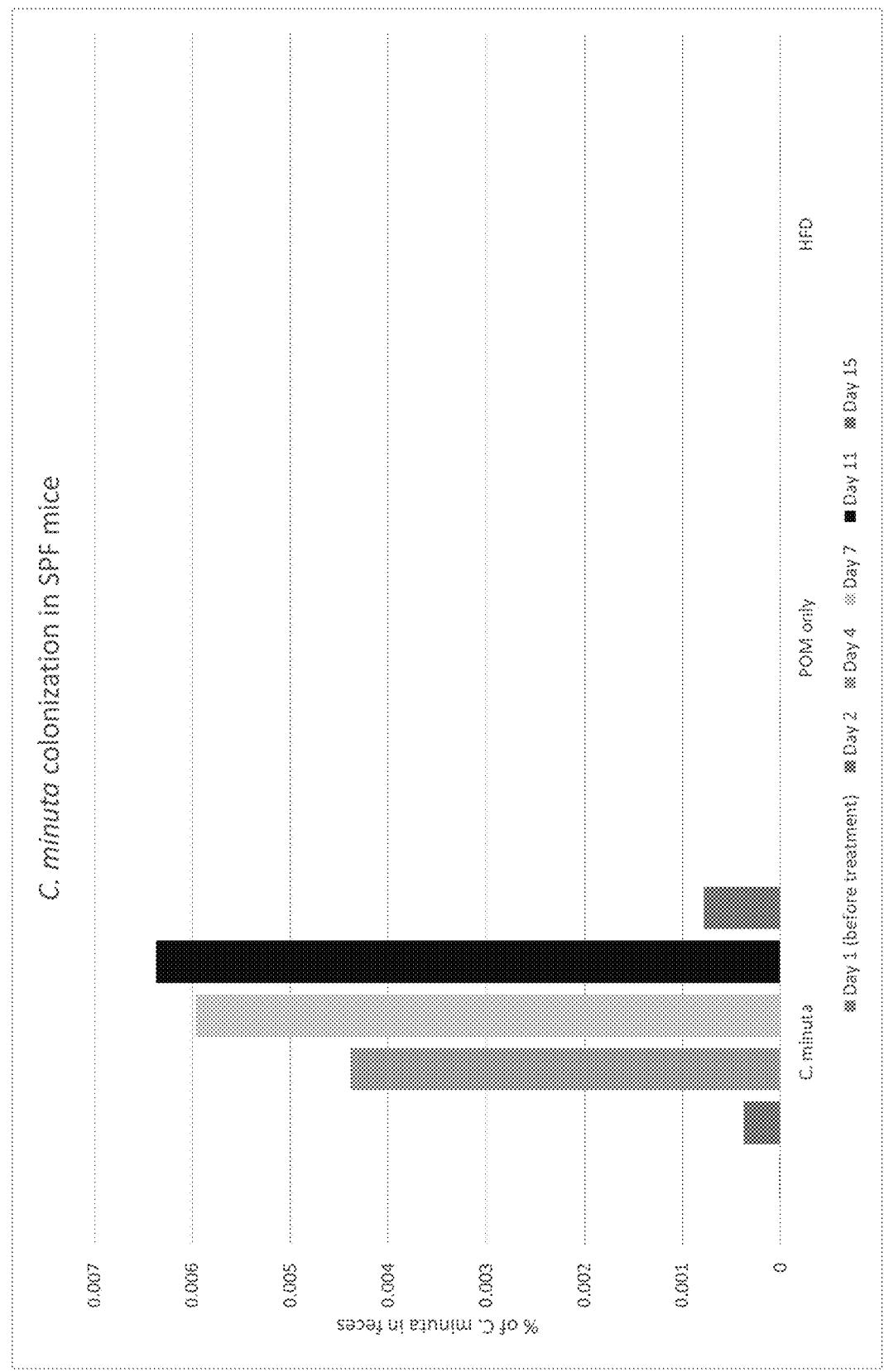
FIG. 9 shows the ability of another biofilm according to some embodiments of the present invention to colonize the gut of an animal model

SPF mice were administered $2*10^7$ *C. minuta* cells in biofilm on pomegranate grains (*C. minuta*), pomegranate grains (POM only) or just diet (HFD) on the first day of the experiment. Feces samples were taken before the probiotic treatment (Day 1), 2 days, 4 days, 7 days, 11 days and 15 days following the probiotic treatment and sent to 16S sequencing. The percent of *C. minuta* in the overall population of bacteria in each feces sample was calculated. The results are shown in FIG. 9. These data show that the biofilm comprising *C. minuta* was capable of colonizing the gut of mice for up to 15 days, when the experiment was terminated, as evidenced by the presence of *C. minuta* in fecal samples.

Example 8

Colonization of Murine Gut Using a Composition According to Some Embodiments of the Present Invention—Comparison with Other Methods A biofilm comprising *L. plantarum* was grown according to the conditions outline below, and given to SPF mice once at a concentration of $2*10^9$ bacteria per day, for 5 days. After this time, mice were fed with food alone for a further 5 days.

Figure 10:
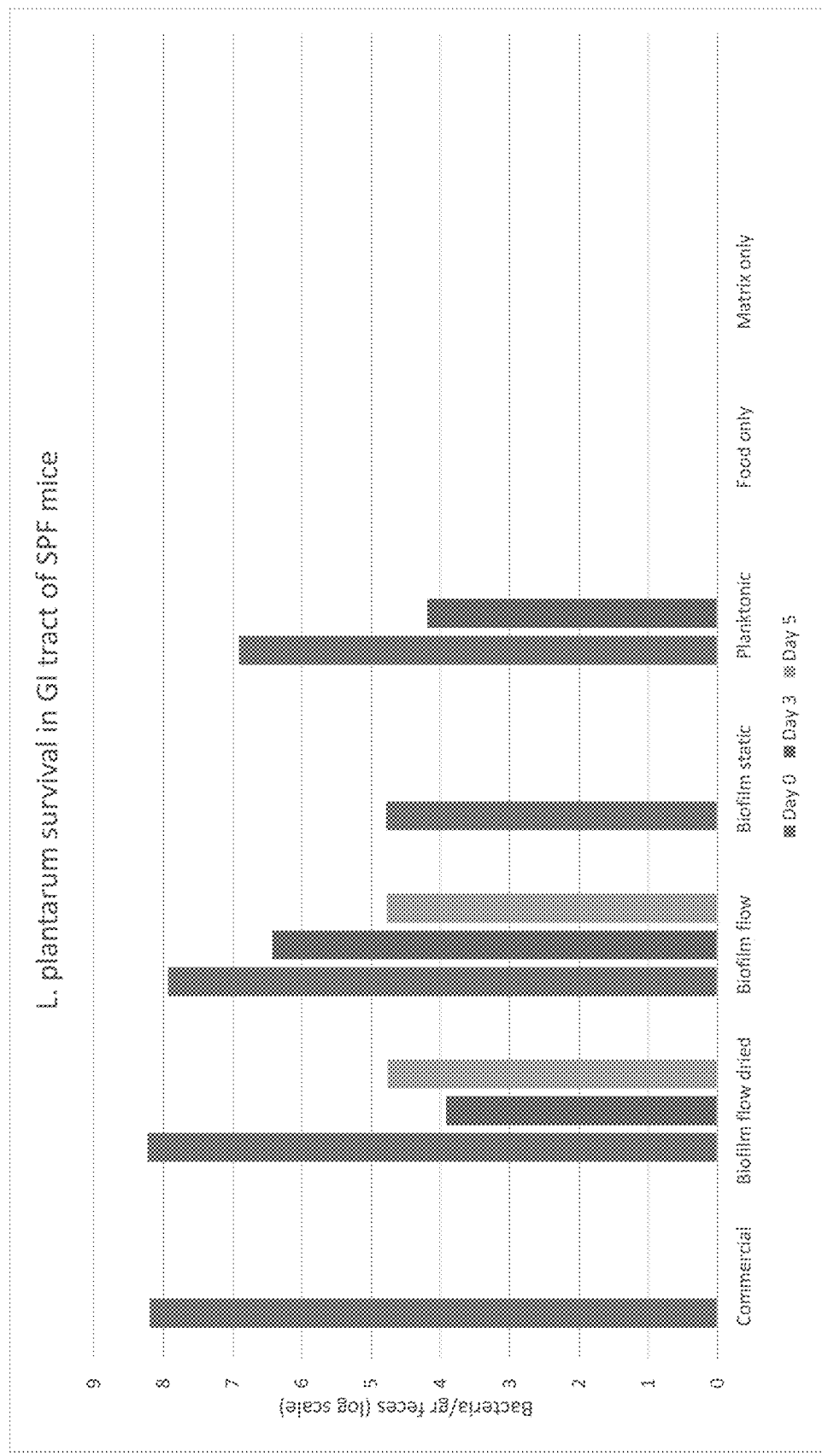
FIG. 10 shows the ability of another biofilm according to some embodiments of the present invention to colonize the gut of an animal model, compared to other biofilms formed using other methods.

The animals were treated as follows (two mice per treatment group):
1. Control—Food only
2. Control—Food with particles (pomegranate grains POM) only.
3. Planktonic. *L. plantarum* was grown overnight in shaking at 37 C in MRS broth.
4. Biofilm static on Pomegranate grains (POM)—5 gr of particles with bacteria (approximately $10^6$ bacteria/day) (according to the methods described in DE202013103204)
5. Biofilm flow on Pomegranate grains (POM)—1.5 gr of particles with bacteria.
6. Biofilm flow on Pomegranate grains (POM) and lyophilized—1.5 gr of particles with bacteria (according to the methods described in Biomacromolecules 2013, 14, 3214-3222).
7. Commercial probiotic supplement—2 pills per day for 5 day The amount of *Lactobacillus* was quantified using colony counts of mice's feces taken at Day 5 (the last day of sample admission), Day 3 and Day 5 (3 and 5 days following cessation of sample admission). The results are shown in FIG. 10. These data show that the biofilm comprising *L. plantarum* formed according to the methods of the present invention was capable of colonizing the gut of mice for up to 5 days, when the experiment was terminated, as evidenced by the presence of *L. plantarum* in fecal samples. However, compositions formed according to the methods described in DE202013103204, or Biomacromolecules 2013, 14, 3214-3222 were not capable of colonizing the gut of mice for up to 5 days.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for treating a subject in need of a probiotic treatment, the method comprising:
providing a probiotic composition comprising a bacterial biofilm comprising a population of at least one bacterial strain attached to a particle; and
administering said probiotic composition to said subject, wherein said bacterial biofilm comprising the population of at least one bacterial strain attached to said particle is produced in a process comprising a step of culturing the population of at least one bacterial strain attached to the particle under anaerobic conditions, thereby treating the subject in need of a probiotic treatment.

2. The method of claim 1, wherein said subject is in need of colonization of the gastrointestinal tract.

3. The method of claim 1, wherein the culturing process comprises the steps of:
   a. inoculation of a population comprising at least one strain of bacteria in a growth medium containing a particle;
   b. incubation of said particle with said population comprising at least one bacterial strain for a time sufficient for the population of at least one strain of bacteria to attach to said particle; and
   c. culturing of the population comprising said at least one strain of bacteria attached to the particles in a growth medium for a time sufficient under anaerobic conditions to form said bacterial biofilm comprising the population of at least one strain of bacteria attached to said particle.

4. The method of claim 3, wherein said growth medium exerts a shear force on the bacteria during the culturing step.

5. The method of claim 1, wherein said particle is a porous particle.

6. The method of claim 1, wherein said particle is ranging from 30 to 500 microns in diameter.

7. The method of claim 1, wherein said particle comprises a plurality of types of particles.

8. The method of claim 1, wherein any one of: said particle is a dicalcium phosphate (DCP) particle.

9. The method of claim 1, wherein said particle is a cellulose particle.

10. The method of claim 1, wherein said particle comprises a plurality of types of particles consisting of DCP particles and cellulose particles.

11. The method of claim 1, wherein said at least one bacterial strain is a gut microflora bacterial strain.

12. The method of claim 1, wherein said particle is a seed.

13. The method of claim 1, wherein said biofilm is further encapsulated with a compound configured to release the at least one bacterial strain in a pH dependent manner.

14. The method of claim 10, wherein said cellulose particles comprise microcrystalline cellulose particles.

15. The method of claim 1, wherein said at least one bacterial strain is selected from the group consisting of: Lactobacillus, Christensenella, and Acetobacter.

16. The method of claim 1, wherein said biofilm comprising at least one bacterial strain attached to a particle is in a lyophilized form.

17. The method of claim 1, wherein said probiotic composition is configured to colonize a gut of said subject for at least five days when ingested by said subject.

18. The method of claim 1, wherein an amount of $2 \times 10^4$ to $2 \times 10^9$ bacteria per day of said bacterial biofilm comprising at least one bacterial strain attached to a particle is configured to colonize a gut of said subject for 1 to 5 days.

* * * * *